(12) United States Patent
Kadow et al.

(10) Patent No.: US 9,932,356 B2
(45) Date of Patent: Apr. 3, 2018

(54) PYRAZOLOPYRIMIDINE MACROCYCLES AS INHIBITORS OF HUMAN IMMUNODEFICIENCY VIRUS REPLICATION

(71) Applicant: VIIV HEALTHCARE UK (No. 5) LIMITED, Brentford, Middlesex (GB)

(72) Inventors: John F. Kadow, Wallingford, CT (US); David R. Langley, Wallingford, CT (US); B. Narasimhulu Naidu, Wallingford, CT (US); Kevin Peese, Wallingford, CT (US); Zhongyu Wang, Wallingford, CT (US)

(73) Assignee: ViiV HEALTHCARE UK (NO. 5) LIMITED, Brentford, Middlesex (GB)

( * ) Notice: Subject to any disclaimer, the term of this patent is extended or adjusted under 35 U.S.C. 154(b) by 57 days.

(21) Appl. No.: 15/115,758

(22) PCT Filed: Feb. 10, 2015

(86) PCT No.: PCT/US2015/015154
§ 371 (c)(1),
(2) Date: Aug. 1, 2016

(87) PCT Pub. No.: WO2015/123182
PCT Pub. Date: Aug. 20, 2015

(65) Prior Publication Data
US 2017/0015683 A1     Jan. 19, 2017

Related U.S. Application Data

(60) Provisional application No. 61/938,959, filed on Feb. 12, 2014.

(51) Int. Cl.
*C07D 513/22*     (2006.01)
*C07D 498/22*     (2006.01)
*C07D 471/22*     (2006.01)

(52) U.S. Cl.
CPC ......... *C07D 513/22* (2013.01); *C07D 471/22* (2013.01); *C07D 498/22* (2013.01)

(58) Field of Classification Search
None
See application file for complete search history.

(56) References Cited

FOREIGN PATENT DOCUMENTS

| WO | WO 2011/076765 A1 | 6/2011 |
|---|---|---|
| WO | WO 2012/033735 A1 | 3/2012 |
| WO | WO 2013/025584 A1 | 2/2013 |
| WO | WO 2013/134113 A1 | 9/2013 |
| WO | WO 2014/028384 A1 | 2/2014 |
| WO | WO 2014/159076 A1 | 10/2014 |
| WO | WO 2014/164428 A1 | 10/2014 |

*Primary Examiner* — Noble E Jarrell
(74) *Attorney, Agent, or Firm* — Robert H. Brink; Edward R. Gimmi; William R. Majarian

(57) ABSTRACT

The disclosure generally relates to compounds of formula I, including compositions and methods for treating human immunodeficiency virus (HIV) infection. The disclosure provides novel inhibitors of HIV, pharmaceutical compositions containing such compounds, and methods for using these compounds in the treatment of HIV infection.

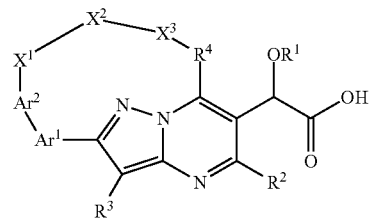

12 Claims, No Drawings

PYRAZOLOPYRIMIDINE MACROCYCLES AS INHIBITORS OF HUMAN IMMUNODEFICIENCY VIRUS REPLICATION

CROSS-REFERENCE TO RELATED APPLICATIONS

This application is a 371 of International Application No.PCT/US 2015/015154, filed 10 Feb. 2015, which claims the benefit of U.S. Provisional Application No. 61/938,959, filed 12 Feb. 2014, which are incorporated herein in their entireties.

BACKGROUND OF THE INVENTION

The disclosure generally relates to compounds, compositions, and methods for the treatment of human immunodeficiency virus (HIV) infection. The disclosure provides novel inhibitors of HIV, pharmaceutical compositions containing such compounds, and methods for using these compounds in the treatment of HIV infection.

Human immunodeficiency virus (HIV) has been identified as the etiological agent responsible for acquired immune deficiency syndrome (AIDS), a fatal disease characterized by destruction of the immune system and the inability to fight off life threatening opportunistic infections. Recent statistics indicate that as many as 35.3 million people worldwide are infected with the virus (UNAIDS Report on the Global AIDS Epidemic 2013). In addition to the large number of individuals already infected, the virus continues to spread. Estimates from 2012 point to close to 2.3 million new infections in that year alone. In the same year there were approximately 1.6 million deaths associated with HIV and AIDS.

There are currently a number of antiviral drugs available to combat the infection. These drugs can be divided into classes based on the viral protein they target or their mode of action. In particular, saquinavir, indinavir, ritonavir, nelfinavir atazanavir darunavir, amprenavir, fosamprenavir, lopinavir and tipranavir are competitive inhibitors of the aspartyl protease expressed by HIV. Zidovudine, didanosine, stavudine, lamivudine, zalcitabine, emtricitibine, tenofovir and abacavir are nucleos(t)ide reverse transcriptase inhibitors that behave as substrate mimics to halt viral cDNA synthesis. The non-nucleoside reverse transcriptase inhibitors nevirapine, delavirdine, efavirenz and etravirine inhibit the synthesis of viral cDNA via a non-competitive (or uncompetitive) mechanism. Enfuvirtide and maraviroc inhibit the entry of the virus into the host cell. An HIV integrase inhibitor, raltegravir (MK-0518, Isentress®), has also been approved for use in treatment experienced patients, and it is clear that this class of inhibitors is very effective as part of a combination regimen containing HIV inhibitors of different classes.

Used alone, these drugs are effective in reducing viral replication: However, the effect is only temporary as the virus readily develops resistance to all known agents used as monotherapy. On the other hand, combination therapy has proven very effective at both reducing virus and suppressing the emergence of resistance in a number of patients. In the US, where combination therapy is widely available, the number of HIV-related deaths has dramatically declined (Palella, F. J.; Delany, K. M.; Moorman, A. C.; Loveless, M. O.; Furher, J.; Satten, G. A.; Aschman, D. J.; Holmberg, S. D. *N. Engl. J. Med.* 1998, 338, 853-860).

Unfortunately, not all patients are responsive and a large number fail this therapy. In fact, initial studies suggest that approximately 30-50% of patients ultimately fail at least one drug in the suppressive combination. Treatment failure in most cases is caused by the emergence of viral resistance. Viral resistance in turn is caused by the replication rate of HIV-1 during the course of infection combined with the relatively high viral mutation rate associated with the viral polymerase and the lack of adherence of HIV-infected individuals in taking their prescribed medications. Clearly, there is a need for new antiviral agents, preferably with activity against viruses already resistant to currently approved drugs. Other important factors include improved safety and a more convenient dosing regimen than many of the currently approved drugs.

Compounds which inhibit HIV replication have been disclosed. See WO2009062288, WO2009062308, WO2010130842, WO2011076765, WO2012003497, WO2012003498, WO2012033735, WO2012140243, WO2013012649, WO2013043553, WO2013073875, WO2013134113, WO2013341142, WO2014021867, WO20140028384, and WO2014164428.

The invention provides technical advantages, for example, the compounds are novel and are useful in the treatment of HIV. Additionally, the compounds provide advantages for pharmaceutical uses, for example, with regard to one or more of their mechanism of action, binding, inhibition efficacy, target selectivity, solubility, safety profiles, or bioavailability.

DESCRIPTION OF THE INVENTION

The invention encompasses compounds of Formula I, including pharmaceutically acceptable salts, their pharmaceutical compositions, and their use in inhibiting HIV integrase and treating those infected with HIV or AIDS.

One aspect of the invention is a compound of Formula I

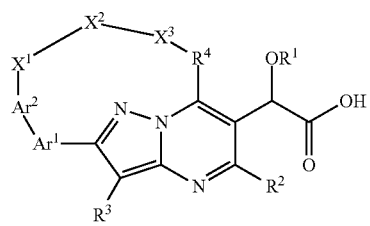

where:
R$^1$ is hydrogen, alkyl, or cycloalkyl;
R$^2$ is hydrogen or alkyl;
R$^3$ is hydrogen, alkyl or halo;
R$^4$ is azetidinyl, pyrrolidinyl, piperidinyl, piperazinyl, morpholinyl, homopiperidinyl, homopiperazinyl, or homomorpholinyl, and is substituted with 0-3 halo or alkyl substituents;
R$^5$ is hydrogen or alkyl;
Ar$^1$ is phenyl substituted with 0-3 substituents selected from cyano, halo, alkyl, haloalkyl, alkoxy, and haloalkoxy;
Ar$^2$ is pyrrolyl, furanyl, thienyl, pyrazolyl, isoxazolyl, isothiazolyl, imidazolyl, oxazolyl, thiazolyl, triazolyl, oxadiazolyl, or thiadiazolyl, and is substituted with 0-3 alkyl substituents;

$X^1$ is CH, $CH_2$, O, S, or $NR^5$;
$X^2$ is alkylene or alkenylene; and
$X^3$ is CH, $CH_2$, $CH_2O$, O, S, or $NR^5$;
or a pharmaceutically acceptable salt thereof.

Another aspect of the invention is a compound of formula I where $R^1$ is alkyl; $R^2$ is alkyl; $R^3$ is hydrogen; $R^4$ is azetidinyl, pyrrolidinyl, piperidinyl, piperazinyl, morpholinyl, homopiperidinyl, homopiperazinyl, or homomorpholinyl substituted with 0-3 alkyl substituents; $Ar^1$ is phenyl substituted with 0-3 substituents selected from cyano, halo, alkyl, haloalkyl, alkoxy, and haloalkoxy; $Ar^2$ is pyrrolyl, furanyl, thienyl, pyrazolyl, isoxazolyl, isothiazolyl, imidazolyl, oxazolyl, thiazolyl, triazolyl, oxadiazolyl, or thiadiazolyl, and is substituted with 0-3 alkyl substituents; $X^1$ is $CH_2$ or O; $X^2$ is alkylene or alkenylene; and $X^3$ is CH, $CH_2$ or O; or a pharmaceutically acceptable salt thereof.

Another aspect of the invention is a compound of formula I where $R^4$ is piperidinyl substituted with 0-1 alkyl substituents; $Ar^1$ is phenyl; $Ar^2$ is pyrazolyl, imidazolyl, or thiazolyl substituted with 0-3 alkyl substituents; $X^1$ is $CH_2$ or O; $X^2$ is alkylene or alkenylene; and $X^3$ is CH, $CH_2$ or O; or a pharmaceutically acceptable salt thereof.

Another aspect of the invention is a compound of formula I where $R^1$ is alkyl, $R^2$ is alkyl and $R^3$ is hydrogen.

Another aspect of the invention is a compound of formula I where $R^4$ is piperidinyl substituted with 0-3 alkyl substituents.

Another aspect of the invention is a compound of formula I where $Ar^1$ is phenyl.

Another aspect of the invention is a compound of formula I where $Ar^2$ is pyrazolyl, imidazolyl, or thiazolyl substituted with 0-3 alkyl substituents.

Another aspect of the invention is a compound of formula I where $X^1$ is $CH_2$ or O; $X^2$ is alkylene or alkenylene; and $X^3$ is CH, $CH_2$ or O.

Another aspect of the invention is a compound of formula I where $X^1$ is $CH_2$; $X^2$ is alkylene or alkenylene; and $X^3$ is $CH_2$.

For a compound of Formula I, the scope of any instance of a variable substituent, including $R^1$, $R^2$, $R^3$, $R^4$, $R^5$, $Ar^1$, $Ar^2$, $X^1$, $X^2$, and $X^3$, can be used independently with the scope of any other instance of a variable substituent. As such, the invention includes combinations of the different aspects.

Unless specified otherwise, these terms have the following meanings. "Alkyl" means a straight or branched alkyl group composed of 1 to 6 carbons. "Alkenyl" means a straight or branched alkyl group composed of 2 to 6 carbons with at least one double bond. "Alkylene" means a straight or branched divalent alkyl group composed of 1 to 6 carbons. "Alkenylene" means a straight or branched divalent alkene group composed of 2 to 6 carbons with at least one double bond. "Cycloalkyl" means a monocyclic ring system composed of 3 to 7 carbons. "Hydroxyalkyl," "alkoxy" and other terms with a substituted alkyl moiety include straight and branched isomers composed of 1 to 6 carbon atoms for the alkyl moiety. "Alkyleneoxy" means a straight or branched divalent alkyloxy group composed of 1 to 6 carbons, for example, —$CH_2CH_2CH_2O$—. "Alkenyleneoxy" means a straight or branched divalent alkeneoxy group composed of 2 to 6 carbons with at least one double bond, for example, —CH=$CHCH_2O$—. "Halo" includes fluoro, chloro, bromo, and iodo. "Halo" includes all halogenated isomers from monohalo substituted to perhalo substituted in substituents defined with halo, for example, "Haloalkyl" "haloalkoxy", "halophenyl", and "halophenoxy." "Aryl" includes carbocyclic and heterocyclic aromatic substituents.

Substituents which are illustrated by chemical drawing to bond at variable positions on a multiple ring system (for example a bicyclic ring system) are intended to bond to the ring where they are drawn to append. Parenthetic and multiparenthetic terms are intended to clarify bonding relationships to those skilled in the art. For example, a term such as ((R)alkyl) means an alkyl substituent further substituted with the substituent R.

The invention includes all pharmaceutically acceptable salt forms of the compounds. Pharmaceutically acceptable salts are those in which the counter ions do not contribute significantly to the physiological activity or toxicity of the compounds and as such function as pharmacological equivalents. These salts can be made according to common organic techniques employing commercially available reagents. Some anionic salt forms include acetate, acistrate, besylate, bromide, chloride, citrate, fumarate, glucouronate, hydrobromide, hydrochloride, hydroiodide, iodide, lactate, maleate, mesylate, nitrate, pamoate, phosphate, succinate, sulfate, tartrate, tosylate, and xinofoate. Some cationic salt forms include ammonium, aluminum, benzathine, bismuth, calcium, choline, diethylamine, diethanolamine, lithium, magnesium, meglumine, 4-phenylcyclohexylamine, piperazine, potassium, sodium, tromethamine, and zinc.

Some of the compounds of the invention exist in stereoisomeric forms. The invention includes all stereoisomeric forms of the compounds including enantiomers and diastereromers. Methods of making and separating stereoisomers are known in the art. The invention includes all tautomeric forms of the compounds. The invention includes atropisomers and rotational isomers.

The invention is intended to include all isotopes of atoms occurring in the present compounds. Isotopes include those atoms having the same atomic number but different mass numbers. By way of general example and without limitation, isotopes of hydrogen include deuterium and tritium. Isotopes of carbon include $^{13}C$ and $^{14}C$. Isotopically-labeled compounds of the invention can generally be prepared by conventional techniques known to those skilled in the art or by processes analogous to those described herein, using an appropriate isotopically-labeled reagent in place of the non-labeled reagent otherwise employed. Such compounds may have a variety of potential uses, for example as standards and reagents in determining biological activity. In the case of stable isotopes, such compounds may have the potential to favorably modify biological, pharmacological, or pharmacokinetic properties.

Biological Methods

Inhibition of HIV replication: A recombinant NL-RLuc proviral clone was constructed in which a section of the nef gene from NL4-3 was replaced with the *Renilla* Luciferase gene. This virus is fully infectious and can undergo multiple cycles of replication in cell culture. In addition, the luciferous reporter provides a simple and easy method for quantitating the extent of virus growth and consequently, the antiviral activity of test compounds. The plasmid pNLRLuc contains the proviral NL-Rluc DNA cloned into pUC18 at the PvuII site. The NL-RLuc virus was prepared by transfection of 293T cells with the plasmid pNLRLuc. Transfections were performed using the LipofectAMINE PLUS kit from Invitrogen (Carlsbad, Calif.) according to the manufacturer and the virus generated was titered in MT-2 cells. For susceptibility analyses, the titrated virus was used to infect MT-2 cells in the presence of compound, and after 5 days of incubation, cells were processed and quantitated for virus growth by the amount of expressed luciferase. Assay media was RPMI 1640 supplemented with 10% heat inactivated fetal bovine serum (FBS), 100 units/ml penicillin G/100 units/ml streptomycin, 10 mM HEPES buffer pH 7.55 and 2 mM L-glutamine. The results from at least 2 experiments were used to calculate the $EC_{50}$ values. Luciferase was quantitated using the Dual Luciferase kit from Promega (Madison, Wis.). Susceptibility of viruses to compounds was determined by incubation in the presence of serial dilutions of the compound. The 50% effective concentration ($EC_{50}$) was calculated by using the exponential form of the median effect equation where $(Fa)=1/[1+(ED_{50}/drug\ conc.)^m]$ (Johnson V A, Byington R T. Infectivity Assay. In *Techniques in HIV Research*. ed. Aldovini A, Walker B D. 71-76. New York: Stockton Press. 1990). Results are shown in Table 1.

TABLE 1

| Example | $EC_{50}$ μM |
|---------|--------------|
| 1 | 0.087 |
| 2 | 0.049 |
| 3 | 0.026 |
| 4 | 0.014 |
| 5 | 0.004 |
| 6 | 0.007 |
| 7 | 0.007 |
| 8 | 0.007 |
| 9 | 0.009 |
| 10 | 0.007 |

Pharmaceutical Composition and Methods of Use

The compounds of this invention inhibit HIV replication. Accordingly, another aspect of the invention is a method for treating HIV infection in a human patient comprising administering a therapeutically effective amount of a compound of Formula I, or a pharmaceutically acceptable salt thereof, with a pharmaceutically acceptable carrier.

Another aspect of the invention is the use of a compound of formula I in the manufacture of a medicament for the treatment of AIDS or HIV infection.

Another aspect of the invention is a method for treating HIV infection in a human patient comprising the administration of a therapeutically effective amount of a compound of Formula I, or a pharmaceutically acceptable salt thereof, with a therapeutically effective amount of at least one other agent used for treatment of AIDS or HIV infection selected from the group consisting of nucleoside HIV reverse transcriptase inhibitors, non-nucleoside HIV reverse transcriptase inhibitors, HIV protease inhibitors, HIV fusion inhibitors, HIV attachment inhibitors, CCR5 inhibitors, CXCR4 inhibitors, HIV budding or maturation inhibitors, and HIV integrase inhibitors.

Another aspect of the invention is a method wherein the agent is a nucleoside HIV reverse transcriptase inhibitor.

Another aspect of the invention is a method wherein the nucleoside HIV reverse transcriptase inhibitor is selected from the group consisting of abacavir, didanosine, emtricitabine, lamivudine, stavudine, tenofovir, zalcitabine, and zidovudine, or a pharmaceutically acceptable salt thereof.

Another aspect of the invention is a method wherein the agent is a non-nucleoside HIV reverse transcriptase inhibitor.

Another aspect of the invention is a method wherein the non-nucleoside HIV reverse transcriptase inhibitor is selected from the group consisting of delavirdine, efavirenz, and nevirapine, or a pharmaceutically acceptable thereof.

Another aspect of the invention is a method wherein the agent is an HIV protease inhibitor.

Another aspect of the invention is a method wherein the HIV protease inhibitor is selected from the group consisting of amprenavir, atazanavir, indinavir, lopinavir, nelfinavir, ritonavir, saquinavir and fosamprenavir, or a pharmaceutically acceptable salt thereof.

Another aspect of the invention is a method wherein the agent is an HIV fusion inhibitor.

Another aspect of the invention is a method wherein the HIV fusion inhibitor is enfuvirtide or T-1249, or a pharmaceutically acceptable salt thereof.

Another aspect of the invention is a method wherein the agent is an HIV attachment inhibitor.

Another aspect of the invention is a method wherein the agent is a CCR5 inhibitor.

Another aspect of the invention is a method wherein the CCR5 inhibitor is selected from the group consisting of Sch-C, Sch-D, TAK-220, PRO-140, and UK-427,857, or a pharmaceutically acceptable salt thereof.

Another aspect of the invention is a method wherein the agent is a CXCR4 inhibitor.

Another aspect of the invention is a method wherein the CXCR4 inhibitor is AMD-3100, or a pharmaceutically acceptable salt thereof.

Another aspect of the invention is a method wherein the agent is an HIV budding or maturation inhibitor.

Another aspect of the invention is a method wherein the budding or maturation inhibitor is PA-457, or a pharmaceutically acceptable salt thereof.

Another aspect of the invention is a method wherein the agent is an HIV integrase inhibitor.

Another aspect of the invention is a pharmaceutical composition comprising a therapeutically effective amount of a compound of Formula I, or a pharmaceutically acceptable salt thereof, with at least one other agent used for treatment of AIDS or HIV infection selected from the group consisting of nucleoside HIV reverse transcriptase inhibitors, non-nucleoside HIV reverse transcriptase inhibitors, HIV protease inhibitors, HIV fusion inhibitors, HIV attachment inhibitors, CCR5 inhibitors, CXCR4 inhibitors, HIV budding or maturation inhibitors, and HIV integrase inhibitors, and a pharmaceutically acceptable carrier.

Another aspect of the invention is the composition wherein the agent is a nucleoside HIV reverse transcriptase inhibitor.

Another aspect of the invention is the composition wherein the nucleoside HIV transcriptase inhibitor is selected from the group consisting of abacavir, didanosine, emtricitabine, lamivudine, stavudine, tenofovir, zalcitabine, and zidovudine, or a pharmaceutically acceptable salt thereof.

Another aspect of the invention is the composition wherein the agent is a non-nucleoside HIV reverse transcriptase inhibitor.

Another aspect of the invention is the composition wherein the non-nucleoside HIV reverse transcriptase inhibitor is selected from the group consisting of delavirdine, efavirenz, and nevirapine, or a pharmaceutically acceptable salt thereof.

Another aspect of the invention is the composition wherein the agent is an HIV protease inhibitor.

Another aspect of the invention is the composition wherein the HIV protease inhibitor is selected from the group consisting of amprenavir, atazanavir, indinavir, lopinavir, nelfinavir, ritonavir, saquinavir and fosamprenavir, or a pharmaceutically acceptable salt thereof.

Another aspect of the invention is the composition wherein the agent is an HIV fusion inhibitor.

Another aspect of the invention is the composition method wherein the HIV fusion inhibitor is enfuvirtide or T-1249, or a pharmaceutically acceptable salt thereof.

Another aspect of the invention is the composition wherein the agent is an HIV attachment inhibitor.

Another aspect of the invention is the composition wherein the agent is a CCR5 inhibitor.

Another aspect of the invention is the composition wherein the CCR5 inhibitor is selected from the group consisting of Sch-C, Sch-D, TAK-220, PRO-140, and UK-427,857, or a pharmaceutically acceptable salt thereof.

Another aspect of the invention is a method wherein the agent is a CXCR4 inhibitor.

Another aspect of the invention is a method wherein the CXCR4 inhibitor is AMD-3100 or a pharmaceutically acceptable salt thereof.

Another aspect of the invention is the composition wherein the agent is an HIV budding or maturation inhibitor.

Another aspect of the invention is the composition wherein the budding or maturation inhibitor is PA-457, or a pharmaceutically acceptable salt thereof.

Another aspect of the invention is the composition wherein the agent is an HIV integrase inhibitor.

"Combination," "coadministration," "concurrent" and similar terms referring to the administration of a compound of Formula I with at least one anti-HIV agent mean that the components are part of a combination antiretroviral therapy or highly active antiretroviral therapy (HAART) as understood by practitioners in the field of AIDS and HIV infection.

"Therapeutically effective" means the amount of agent required to provide a meaningful patient benefit as understood by practitioners in the field of AIDS and HIV infection. In general, the goals of treatment are suppression of viral load, restoration and preservation of immunologic function, improved quality of life, and reduction of HIV-related morbidity and mortality.

"Patient" means a person infected with the HIV virus and suitable for therapy as understood by practitioners in the field of AIDS and HIV infection.

"Treatment," "therapy," "regimen," "HIV infection," "ARC," "AIDS" and related terms are used as understood by practitioners in the field of AIDS and HIV infection.

The compounds of this invention are generally given as pharmaceutical compositions comprised of a therapeutically effective amount of a compound of Formula I or its pharmaceutically acceptable salt and a pharmaceutically acceptable carrier and may contain conventional excipients. A therapeutically effective amount is that which is needed to provide a meaningful patient benefit. Pharmaceutically acceptable carriers are those conventionally known carriers having acceptable safety profiles. Compositions encompass all common solid and liquid forms including capsules, tablets, lozenges, and powders as well as liquid suspensions, syrups, elixers, and solutions. Compositions are made using common formulation techniques, and conventional excipients (such as binding and wetting agents) and vehicles (such as water and alcohols) are generally used for compositions. See, for example, *Remington's Pharmaceutical Sciences*, 17th edition, Mack Publishing Company, Easton, Pa. (1985).

Solid compositions are normally formulated in dosage units and compositions providing from about 1 to 1000 mg of the active ingredient per dose are preferred. Some examples of dosages are 1 mg, 10 mg, 100 mg, 250 mg, 500 mg, and 1000 mg. Generally, other antiretroviral agents will be present in a unit range similar to agents of that class used clinically. Typically, this is 0.25-1000 mg/unit.

Liquid compositions are usually in dosage unit ranges. Generally, the liquid composition will be in a unit dosage range of 1-100 mg/mL. Some examples of dosages are 1 mg/mL, 10 mg/mL, 25 mg/mL, 50 mg/mL, and 100 mg/mL. Generally, other antiretroviral agents will be present in a unit range similar to agents of that class used clinically. Typically, this is 1-100 mg/mL.

The invention encompasses all conventional modes of administration; oral and parenteral methods are preferred. Generally, the dosing regimen will be similar to other antiretroviral agents used clinically. Typically, the daily dose will be 1-100 mg/kg body weight daily. Generally, more compound is required orally and less parenterally. The specific dosing regime, however, will be determined by a physician using sound medical judgement.

The invention also encompasses methods where the compound is given in combination therapy. That is, the compound can be used in conjunction with, but separately from, other agents useful in treating AIDS and HIV infection. Some of these agents include HIV attachment inhibitors, CCR5 inhibitors, CXCR4 inhibitors, HIV cell fusion inhibitors, HIV integrase inhibitors, HIV nucleoside reverse transcriptase inhibitors, HIV non-nucleoside reverse transcriptase inhibitors, HIV protease inhibitors, budding and maturation inhibitors, immunomodulators, and anti-infectives. In these combination methods, the compound of Formula I will generally be given in a daily dose of 1-100 mg/kg body weight daily in conjunction with other agents. The other agents generally will be given in the amounts used therapeutically. The specific dosing regime, however, will be determined by a physician using sound medical judgement.

Synthetic Methods

The compounds of this invention can be made by various methods known in the art including those of the following schemes and in the specific embodiments section. The structure numbering and variable numbering shown in the synthetic schemes are distinct from, and should not be confused with, the structure or variable numbering in the claims or the rest of the specification. The variables in the schemes are meant only to illustrate how to make some of the compounds of this invention. The disclosure is not limited to the foregoing illustrative examples and the examples should be considered in all respects as illustrative and not restrictive, reference being made to the appended claims, rather than to the foregoing examples, and all changes which come within the meaning and range of equivalency of the claims are therefore intended to be embraced.

Abbreviations used in the schemes and examples generally follow conventions used in the art. Chemical abbreviations used in the specification and examples are defined as follows: "KHMDS" for potassium bis(trimethylsilyl)amide; "DMF" for N,N-dimethylformamide; "HATU" for O-(t-Azabenzotriazo1-1-yl)-N,N,N',N'-tetramethyluronium hexafluorophosphate, "MeOH" for methanol; "Ar" for aryl; "TFA" for trifluoroacetic acid, "DMSO" for dimethylsulfoxide; "h" for hours; "rt" for room temperature or retention time (context will dictate); "min" for minutes; "EtOAc" for ethyl acetate; "THF" for tetrahydrofuran; "Et$_2$O" for diethyl ether; "DMAP" for 4-dimethylaminopyridine; "DCM" for dichloromethane, "DCE" for 1,2-dichloroethane; "ACN" for acetonitrile; "DME" for 1,2-dimethoxyethane; "HOBt" for 1-hydroxybenzotriazole hydrate; "DIEA" for diisopropylethylamine, "DEAD" for diethyl azodicarboxylate and "DIAD" for diisopropyl azodicarboxylate.

Abbreviations as used herein, are defined as follows: "1×" for once, "2×" for twice, "3×" for thrice, "° C." for degrees Celsius, "eq" for equivalent or equivalents, "g" for gram or grams, "mg" for milligram or milligrams, "L" for liter or liters, "mL" for milliliter or milliliters, "μL" for microliter or microliters, "N" for normal, "M" for molar, "mmol" for millimole or millimoles, "atm" for atmosphere, "psi" for pounds per square inch, "conc." for concentrate, "sat" or "sat'd" for saturated, "MW" for molecular weight, "mp" for melting point, "ee" for enantiomeric excess, "MS" or "Mass Spec" for mass spectrometry, "ESI" for electrospray ionization mass spectroscopy, "HR" for high resolution, "HRMS" for high resolution mass spectrometry, "LCMS" for liquid chromatography mass spectrometry, "HPLC" for high pressure liquid chromatography, "RP HPLC" for reverse phase HPLC, "TLC" or "tlc" for thin layer chromatography, "NMR" for nuclear magnetic resonance spectroscopy, "$^1$H" for proton, "δ" for delta, "s" for singlet, "d" for doublet, "t" for triplet, "q" for quartet, "m" for multiplet, "br" for broad, "Hz" for hertz, and "α", "β", "R", "S", "E", and "Z" are stereochemical designations familiar to one skilled in the art.

Some compounds can be synthesized from an appropriately substituted heterocycle I-1 according to Scheme I, Compound I-1 and I-2 are commercially available or synthesized by reactions known in the art. Intermediates I-3 could be prepared by procedure known in the art or as set forth in the examples below using compound I-1 and compound I-2. Intermediates I-3 could be transformed to intermediates I-4 using conditions known to those skilled in the art. Intermediates I-4 could be oxidized to intermediates I-5 by reactions known in the art, including Davis oxidation. Intermediates I-5 could be oxidized to intermediates I-6 by known conditions, including Dess-Martin oxidation. Intermediates I-6 could be reduced to chiral intermediates I-7 using known conditions in the presence of catalytic chiral Lewia acids. Intermediates I-7 could be converted to the intermediates I-8 by known conditions, including tertiary-butyl acetate and perchloric acid. Coupling of appropriate amines with intermediates I-8 would provide intermediates I-9. Coupling of aryl group to intermediates I-9 using conditions known in the art, including Suzuki coupling, would give intermediates I-10. Boronate or boronic acid coupling reagents are commercially available or are prepared by reactions known in the art (for example, PCT Appln. WO20090662285). Intermediates I-10 could be converted to intermediates I-11 by conditions known in the art, including ring closing metathesis. Hydrolysis of intermediates I-11 would provide products I-12 which could be converted to I-13 using conditions known in the art.

Scheme I.

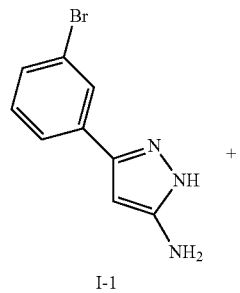

I-1

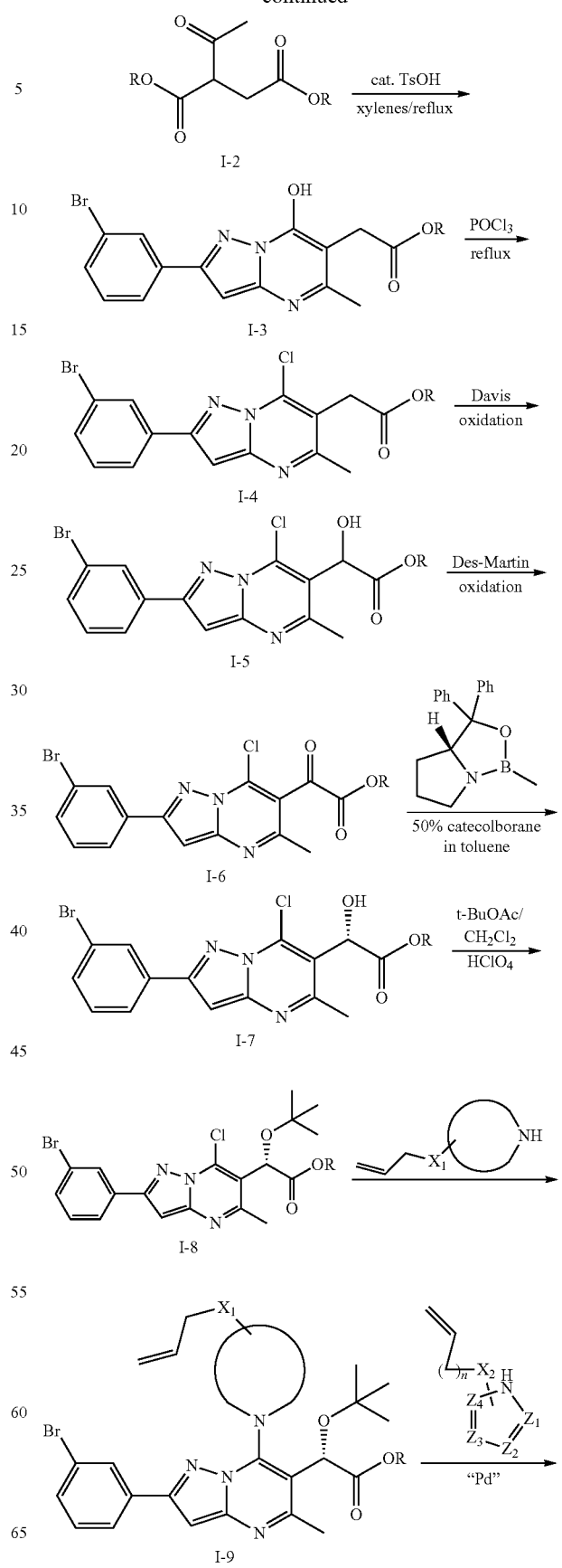

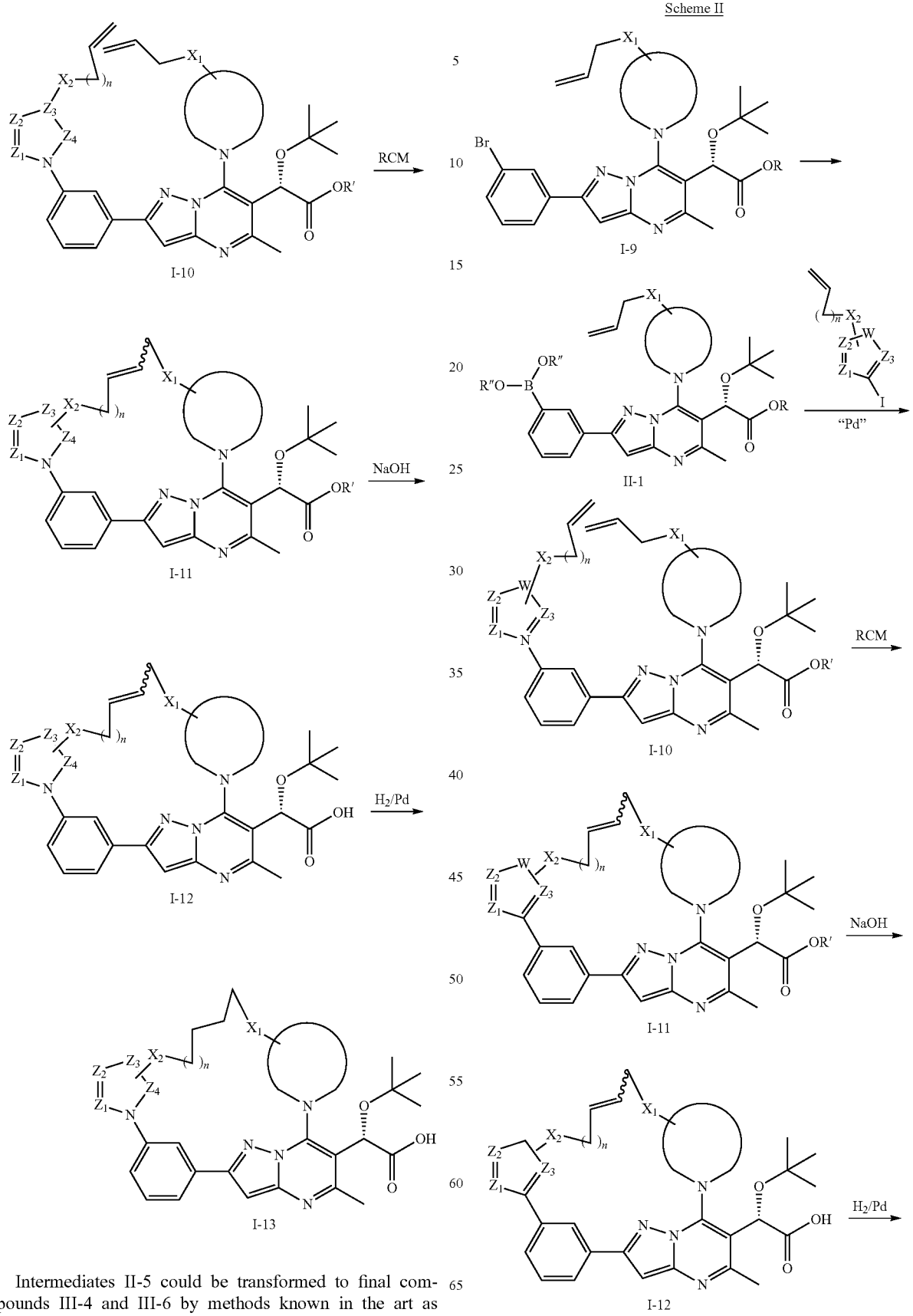
Intermediates II-5 could be transformed to final compounds III-4 and III-6 by methods known in the art as outlined in Scheme II.

-continued

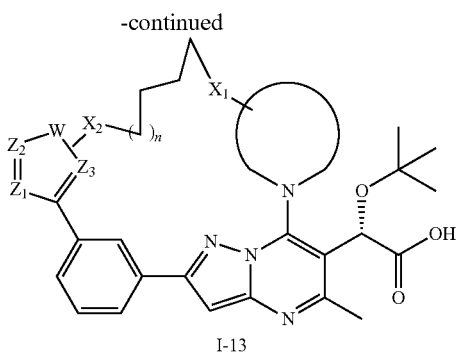

I-13

The compounds described herein were purified by the methods known to those skilled in art by normal phase column chromatography on silica gel column using appropriate solvent systems. Preparative HPLC purifications mentioned in this experimentation section were carried out by gradient elution on C18 prep-columns (5 μm) using either mobile phase A:9:1 H₂O/acetonitrile with 10 mM NH₄OAc and mobile phase B:A:9:1 acetonitrile/H₂O with: 10 mM NH₄OAc or mobile phase A: 95:5 H₂O/MeOH with 20 mM NH₄OAc and mobile phase B:95:5 MeOH/H₂O with 20 mM NH₄OAc.

Intermediate 1

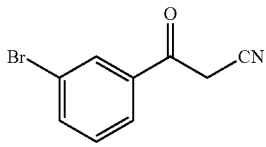 [SMILES: N#CCC(=O)c1cccc(Br)c1]

3-(3-bromophenyl)-3-oxopropanenitrile: Acetonitrile (21.86 mL, 419 mmol) was added to a stirred suspension of 60% NaH (7.25 g, 181 mmol) in THF (150 mL). Then, methyl 3-bromobenzoate (30 g, 140 mmol) was added and the mixture was heated at 75° C. for 4 h. After cooling to room temperature, water followed by 1N HCl (200 mL) was added and the mixture was extracted with ethyl acetate (500 mL), washed with sat.NaHCO₃ solution (200 mL), dried (Na₂SO₄), filtered and concentrated to afford 3-(3-bromophenyl)-3-oxopropanenitrile (29 g, 129 mmol, 93% yield) as light yellow solid. $^1$H NMR (500 MHz, CDCl₃) δ 8.09 (t, J=1.7 Hz, 1H), 7.90-7.86 (m, 1H), 7.83 (ddd, J=8.0, 2.0, 1.1 Hz, 1H), 7.45 (t, J=7.9 Hz, 1H), 4.08 (s, 2H).

Intermediate 2

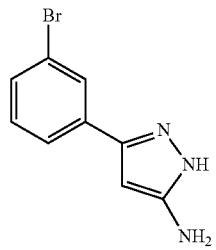 [SMILES: Nc1cc(-c2cccc(Br)c2)n[nH]1]

3-(3-bromophenyl)-1H-pyrazol-5-amine: A mixture of 3-(3-bromophenyl)-3-oxopropanenitrile (35 g, 156 mmol) and hydrazine hydrate (11.34 mL, 234 mmol) in ethanol (600 mL) was refluxed for 16 h. Mixture was then cooled and concentrated in vacuuo. Crude product was diluted with dichloromethane and stirred for 5 min. Solids were filtered and dried to afford 3-(3-bromophenyl)-1H-pyrazol-5-amine (30 g, 126 mmol, 81% yield) as off-white solid. $^1$H NMR (400 MHz, DMSO-d₆) δ 12.02 (br. s., 0.4H), 11.66 (br. s., 0.6H), 7.86 (t, J=1.6 Hz, 1H), 7.67 (d, J=7.5 Hz, 1H), 7.45 (d, J=6.8 Hz, 1H), 7.37-7.18 (m, 1H), 5.78 (br. s., 1H), 5.08 (br. s., 1.2H), 4.68 (br. s., 0.8H). LCMS (M+H)=240.1.

Intermediate 3

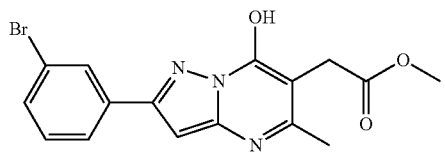 [SMILES: COC(=O)Cc1c(C)nc2cc(-c3cccc(Br)c3)nn2c1O]

Methyl 2-(2-(3-bromophenyl)-7-hydroxy-5-methylpyrazolo[1,5-a]pyrimidin-6-yl)acetate: A 3-lit three neck flask was fitted with a mechanical stirrer and a heating mantle. A suspension of 3-(3-bromophenyl)-1H-pyrazol-5-amine (84.9 g, 357 mmol), dimethyl 2-acetylsuccinate (73.8 g, 392 mmol) and tosic acid monohydrate (1.357 g, 7.13 mmol) in o-xylene (1500 mL) was heated to refluxed (135° C. measured internal temp) for 3.5 h. The heating was turned off, the reaction was diluted with hexanes (1000 mL) and was allowed to cool slowly overnight. The solids were collected by filtration. The filter cake was washed with hexanes and dried under vacuum overnight to afford methyl 2-(2-(3-bromophenyl)-7-hydroxy-5-methylpyrazolo [1,5-a]pyrimidin-6-yl)acetate (132.21 g, 334 mmol, 94% yield) as a white powdery solid. $^1$H NMR (500 MHz, DMSO-d₆) δ: 12.47 (s, 1H), 8.18 (t, J=1.7 Hz, 1H), 8.02 (dt, J=7.1, 1.3 Hz, 1H), 7.65-7.60 (m, 1H), 7.45 (t, J=7.9 Hz, 1H), 6.69 (s, 1H), 3.63 (s, 3H), 3.58 (s, 2H), 2.34 (s, 3H). LCMS (M+H)=376.4.

Intermediate 4

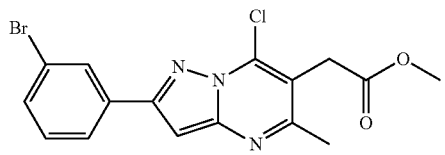 [SMILES: COC(=O)Cc1c(C)nc2cc(-c3cccc(Br)c3)nn2c1Cl]

2-(2-(3-Bromophenyl)-7-chloro-5-methylpyrazolo[1,5-a]pyrimidin-6-yl)acetate: A mixture of methyl 2-(2-(3-bromophenyl)-7-hydroxy-5-methylpyrazolo [1,5-a]pyrimidin-6-yl)acetate (133 g, 354 mmol) and N,N-dimethylaniline (62.7 ml, 495 mmol) in POCl₃ (450 ml) was heated (120° C. oil bath) for 2.5 h. The reaction was cooled, then concentrated under reduced pressure. The residue was dried from toluene (3×300 mL), and the residue, suspended in EtOAc (600 mL) was poured onto ice water at a rate that maintained the cold temperature. The emulsion was then diluted (EtOAc, 300 mL) and the combined layers were pulled through a filter paper to collect solids. The solids were washed with several portions of EtOAc, then air dried. The filtered solids were suspended in EtOAc and hexanes (500 mL of each) and stirred for 10 min, then filtered. The filter cake was washed with hexanes and dried under vacuum to afford methyl 2-(2-(3-bromophenyl)-7-chloro-5-methyl-pyrazolo[1,5-a]pyrimidin-6-yl)acetate (121.7 g, 300 mmol, 85% yield) as pale green solid. $^1$H NMR (500 MHz, DMSO-d$_6$) δ: 8.25 (t, J=1.8 Hz, 1H), 8.09 (dt, J=7.8, 1.3 Hz, 1H), 7.63-7.70 (m, 1H), 7.45-7.54 (m, 1H), 7.40 (s, 1H), 4.04 (s, 2H), 3.71 (s, 3H), 2.58 (s, 3H). LC/MS (085-04, M+H)=396.1.

Intermediate 5

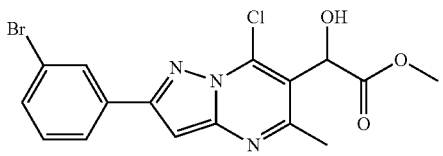 [SMILES: COC(=O)C(O)c1c(C)nc2cc(-c3cccc(Br)c3)nn2c1Cl]

Methyl 2-(2-(3-bromophenyl)-7-chloro-5-methylpyrazolo[1,5-a]pyrimidin-6-yl)-2-hydroxyacetate. To a stirred solution of 0.91M KHMDS/THF (95 mL, 95 mmol) in THF (50 mL) at −78° C. was added dropwise a solution of methyl 2-(2-(3-bromophenyl)-7-chloro-5-methylpyrazolo[1,5-a]pyrimidin-6-yl)acetate (25 g, 63.3 mmol) in THF (300 mL). After 1 h, 3-phenyl-2-(phenylsulfonyl)-1,2-oxaziridine (24.8 g, 95 mmol) in THF (100 mL) was added over the course of 10 min. This red reaction mixture was stirred at −78° C. for 2 h. Then, the resulting orange solution was quenched with sat. aq. NH$_4$Cl (400 mL), diluted with EtOAc (400 mL), and partitioned with a sep. funnel. The organic phase was washed with water and brine. The organic phase was dried (Na$_2$SO$_4$), filtered, and concentrated to give a light brown solid. Trituration with hexanes followed by trituration with ether (5×50 mL) gave 21 g of a yellow solid: methyl 2-(2-(3-bromophenyl)-7-chloro-5-methylpyrazolo[1,5-a]pyrimidin-6-yl)-2-hydroxyacetate (as a 1:1 complex with benzenesulfonamide). $^1$H NMR (400 MHz, CDCl3) δ 8.20 (t, J=1.8 Hz, 1H), 7.95 (dq, J=7.8, 0.8 Hz, 1H), 7.57 (ddd, J=8.0, 2.0, 1.0 Hz, 1H), 7.37 (t, J=7.9 Hz, 1H), 6.95 (s, 1H), 5.79 (s, 1H), 3.87 (s, 3H), 3.59 (d, J=1.8 Hz, 1H), 2.65 (s, 3H). LCMS (M+H)=410 and 412.

Intermediate 6

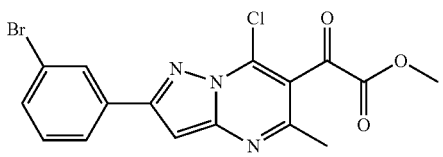 [SMILES: COC(=O)C(=O)c1c(C)nc2cc(-c3cccc(Br)c3)nn2c1Cl]

Methyl 2-(2-(3-bromophenyl)-7-chloro-5-methylpyrazolo[1,5-a]pyrimidin-6-yl)-2-oxoacetate. To a stirred inseparable mixture of methyl 2-(2-(3-bromophenyl)-7-chloro-5-methylpyrazolo[1,5-a]pyrimidin-6-yl)-2-hydroxy-acetate (12.9 g, 31.4 mmol) and benzenesulfonamide (2.96 g, 18.85 mmol) in CH$_2$Cl$_2$ (700 mL) was added Dess-Martin Periodinane (13.3 g, 31.4 mmol). Stir for 60 min at rt at which time the reaction appeared complete by TLC (1:1 hexane/EtOAc). The reaction was placed in the refrigerator for 2 h and then filtered through a medium fritted glass funnel. The brown homogeneous solution was treated with 140 mL of sat.aq. Na$_2$CO$_3$ and stirred rapidly for 30 min. The organic phase was separated and washed with additional sat.aq. Na$_2$CO$_3$ in a separatory funnel. The organic phase was dried (Na$_2$SO$_4$) and filtered through celite. The filtrate was then filtered through 170 g of silica gel with the aid of another 1 L of CH$_2$Cl$_2$. The light yellow filtrate was concentrated in vacuo to give 9.5 g of a yellow solid which after further drying gave 8.43 g (66%) of methyl 2-(2-(3-bromophenyl)-7-chloro-5-methylpyrazolo[1,5-a]pyrimidin-6-yl)-2-oxoacetate as a light yellow solid. $^1$H NMR (400 MHz, CDCl3) δ 8.21 (t, J=1.6 Hz, 1H), 7.96 (d, J=7.8 Hz, 1H), 7.60 (dt, J=8.0, 0.9 Hz, 1H), 7.39 (t, J=7.9 Hz, 1H), 7.02 (s, 1H), 4.03 (s, 3H), 2.65 (s, 3H). LCMS (M+H)=408 and 410.

Intermediate 7

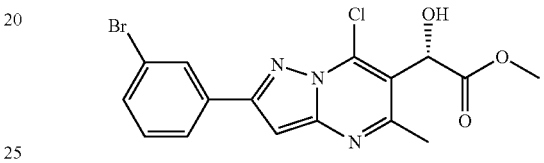

(S)-Methyl 2-(2-(3-bromophenyl)-7-chloro-5-methyl-pyrazolo[1,5-a]pyrimidin-6-yl)-2-hydroxyacetate. To a stirred solution of methyl 2-(2-(3-bromophenyl)-7-chloro-5-methylpyrazolo[1,5-a]pyrimidin-6-yl)-2-oxoacetate (14 g, 34.3 mmol) in anhydrous toluene (400 mL) was added 1.1M (R)-1-methyl-3,3-diphenylhexahydropyrrolo[1,2-c][1,3,2] oxazaborole/toluene (12.5 mL, 13.7 mmol). The mixture was cooled to −35° C. and then a 4.17M solution of catechoborane/toluene (11.7 mL, 48 mmol) was added over the course of 10 min. After 30 min, the reaction mixture was slowly warmed to −15° C and stirred for additional 2 h. At this point the reaction mixture was diluted with EtOAc (300 mL) and treated with sat.aq. Na$_2$CO$_3$ (50 mL). The mixture was stirred vigorously for 10 min. The organic phase was separated and washed with sat. aq. Na$_2$CO$_3$ (5×100 mL), 0.1N HCl (1×100 mL), and brine. The organic phase was dried (Na$_2$SO$_4$), filtered, and concentrated. The residue was triturated with ether to obtain 12 g (77%) of the desired (S)-methyl 2-(2-(3-bromophenyl)-7-chloro-5-methylpyrazolo[1,5-a]pyrimidin-6-yl)-2-hydroxyacetate as a colorless oil. $^1$H NMR (400 MHz, CDCl$_3$) δ 8.20 (t, J=1.8 Hz, 1H), 7.95 (dq, J=7.8, 0.8 Hz, 1H), 7.57 (ddd, J=8.0, 2.0, 1.0 Hz, 1H), 7.37 (t, J=7.9 Hz, 1H), 6.95 (s, 1H), 5.79 (s, 1H), 3.87 (s, 3H), 3.59 (d, J=1.8 Hz, 1H), 2.65 (s, 3H). LCMS (M+H)=410 and 412.

Intermediate 8

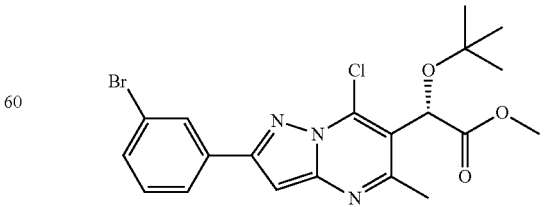

(S)-Methyl 2-(2-(3-bromophenyl)-7-chloro-5-methyl-pyrazolo[1,5-a]pyrimidin-6-yl)-2-(tert-butoxy)acetate. A mixture of (S)-methyl 2-(2-(3-bromophenyl)-7-chloro-5-methylpyrazolo[1,5-a]pyrimidin-6-yl)-2-hydroxyacetate (7.81 g, 19.02 mmol), t-butylacetate (160 mL) in DCM (330 mL) was added perchloric acid (3.43 mL, 57.1 mmol) and the mixture was stirred at rt for 3 h. It was then quenched with sat.aq.NaHCO₃ (adjusted to pH=7-8 by the addition of solid NaHCO₃). This mixture was diluted with EtOAc and the organic phase was washed with water. The organic phase was dried (MgSO₄), filtered, and concentrated in vacuo to obtain ~7 g of crude product as an oil. Filtration through 70 g of silica gel eluting with CH₂Cl₂ gave (S)-methyl 2-(2-(3-bromophenyl)-7-chloro-5-methylpyrazolo[1,5-a]pyrimidin-6-yl)-2-(tert-butoxy)acetate (5.71 g, 12.23 mmol, 64.3% yield). ¹H NMR (400 MHz, CDCl₃) δ 8.20 (t, J=1.6 Hz, 1H), 7.95 (dt, J=7.8, 1.1 Hz, 1H), 7.63-7.53 (m, 1H), 7.37 (t, J=7.9 Hz, 1H), 6.94 (s, 1H), 5.69 (s, 1H), 3.76 (s, 3H), 2.70 (s, 3H), 1.30 (s, 9H). LCMS (M+H)=466 and 468.

Intermediate 9

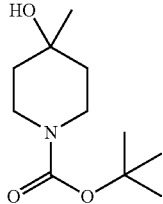

tert-Butyl 4-hydroxy-4-methylpiperidine-1-carboxylate: Under an N₂ atmosphere, a 3N MeMgBr/ether (1.67 mL, 5.02 mmol) was added dropwise to a cooled (−25° C.) solution of tert-butyl 4-hydroxy-4-methylpiperidine-1-carboxylate (4 g, 20.08 mmol) in ether (20 mL). The reaction mixture was allowed to warm to rt and was stirred for 2 h. It was then cooled to 0° C. and quenched by the addition of sat. NH₄Cl. Another 20 mL of ether was added and the mixture was partitioned in a separatory funnel. The organic phase was set aside and the aqueous phase was extracted with another 20 mL of ether. The combined ether extracts were dried over MgSO₄, filtered and evaporated to obtain an oil, which was then purified by biotage, eluting with 0-50% EtOAc/hexane to obtain tert-butyl 4-hydroxy-4-methylpiperidine-1-carboxylate (4.30 g, 18.0 mmol, 90% yield) as a colorless oil. 1H NMR (500 MHz, CDCl₃) δ 3.84-3.65 (m, 2H), 3.34-3.18 (m, 2H), 2.59-2.39 (m, 1H), 1.61-1.53 (m, 4H), 1.50-1.45 (m, 9H), 1.32-1.27 (m, 3H).

Intermediate 10

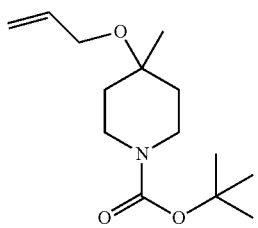 [SMILES: C=CCOC1(C)CCN(C(=O)OC(C)(C)C)CC1]

tert-Butyl 4-(allyloxy)-4-methylpiperidine-1-carboxylate: To a mixture of tert-butyl 4-hydroxy-4-methylpiperidine-1-carboxylate (4.30 g, 20.0 mmol) in DMF (50 mL) at 0° C. was added NaH (60 wt %) (1.60 g, 39.9 mmol). The mixture was then stirred at rt for 2 h. At this time allyl bromide (8.64 mL, 100 mmol) was added slowly over the course of 5 min. The reaction mixture was stirred at rt for 3 h. It was then cooled to 0° C. and quenched with sat. NH₄Cl. The reaction mixture was extracted with ether. The organic phase was dried over MgSO₄, filtered and concentrated to obtain a colorless oil, which was then purified by biotage, eluting with 0-25% EtOAc/hexane to isolate 3.1 g (61%) of tert-butyl 4-(allyloxy)-4-methylpiperidine-1-carboxylate as a colorless oil. ¹H NMR (500 MHz, CDCl₃) δ 6.02-5.90 (m, 1H), 5.32 (dd, J=17.2, 1.7 Hz, 1H), 5.16 (dd, J=10.4, 1.4 Hz, 1H), 3.94-3.88 (m, 2H), 3.73 (br. s., 2H), 3.19 (br. s., 2H), 1.78 (d, J=13.1 Hz, 2H), 1.53-1.42 (m, 11H), 1.21 (s, 3H).

Intermediate 11

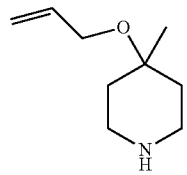

4-(Allyloxy)-4-methylpiperidine hydrochloride: A mixture of tert-butyl 4-(allyloxy)-4-methylpiperidine-1-carboxylate (3.10 g, 12.1 mmol) and 4N HCl/dioxane (15 mL, 60.0 mmol) was stirred at rt for 3 h. It was then concentrated in vacuum to obtain 2.2 g (95%) of 4-(allyloxy)-4-methylpiperidine hydrochloride as a light brown solid. ¹H NMR (500 MHz, METHANOL-d₄) δ 6.02-5.92 (m, 1H), 5.33 (dd, J=17.2, 1.7 Hz, 1H), 5.15 (dd, J=10.6, 1.7 Hz, 1H), 3.96 (dt, J=5.1, 1.6 Hz, 2H), 3.23-3.18 (m, 4H), 2.06 (dd, J=15.3, 2.5 Hz, 2H), 1.77-1.69 (m, 2H), 1.31-1.28 (s, 3H).

Intermediate 12

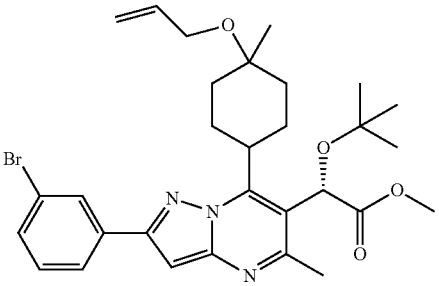 [SMILES: C=CCOC1(C)CCC(c2c([C@H](OC(C)(C)C)C(=O)OC)c(C)nc3cc(-c4cccc(Br)c4)nn23)CC1]

(S)-Methyl 2-(7-(4-(allyloxy)-4-methylpiperidin-1-yl)-2-(3-bromophenyl)-5-methylpyrazolo[1,5-a]pyrimidin-6-yl)-2-(tert-butoxy)acetate. (S)-methyl 2-(2-(3-bromophenyl)-7-chloro-5-methylpyrazolo[1,5-a]pyrimidin-6-yl)-2-(tert-butoxy)acetate (10.9 g, 23.3 mmol) was dissolved in DMF (100 mL). After flushing with N₂, 4-(allyloxy)-4-methylpiperidine.HCl (7.34 g, 35.0 mmol) and Hunig's Base (12.22 mL, 70.0 mmol) were added to the reaction mixture. After stirring for 18 h at rt, the reaction was heated at 50° C. for 3 h to complete the reaction. The reaction mixture was concentrated in vacuo at 50° C. to remove most of the DMF. The residue was partitioned between EtOAc and 0.01N HCl. The organic phase was washed with water and brine. Then, the organic phase was dried (MgSO$_4$), filtered, and concentrated in vacuo. The residue was dissolved in about 600 mL of hot hexanes and cooled for 18 h in the freezer to give a crystalline solid. Filtration gave 6.5 g of (S)-methyl 2-(7-(4-(allyloxy)-4-methylpiperidin-1-yl)-2-(3-bromophenyl)-5-methylpyrazolo[1,5-a]pyrimidin-6-yl)-2-(tert-butoxy)acetate. The filtrate was purified by Biotage (10-50% EtOAc) to give another 5.71 g of (S)-methyl 2-(7-(4-(allyloxy)-4-methylpiperidin-1-yl)-2-(3-bromophenyl)-5-methylpyrazolo[1,5-a]pyrimidin-6-yl)-2-(tert-butoxy)acetate. The combined yield of the desired product was 12.21 g (89%). $^1$H NMR (400 MHz, METHANOL-d$_4$) δ 8.23 (t, J=1.8 Hz, 1H), 8.01 (dt, J=7.8, 1.3 Hz, 1H), 7.60-7.55 (m, 1H), 7.43-7.37 (m, 1H), 6.90 (s, 1H), 6.18-5.95 (m, 2H), 5.48 (d, J=17.3 Hz, 1H), 5.25 (d, J=10.0 Hz, 1H), 4.11-4.06 (m, 2H), 3.77 (s, 3H), 2.59 (s, 3H), 2.14-1.95 (m, 3H), 1.82-1.71 (m, 1H), 1.37 (s, 3H), 1.28 (s, 9H). LCMS (M+H)=585 and 587.

Intermediate 13

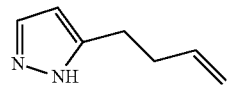

5-(But-3-en-1-yl)-1H-pyrazole: Hex-5-en-2-one (1.189 mL, 10.19 mmol, 1 equiv) and 1-tert-butoxy-N,N,N',N'-tetramethylmethanediamine (3.16 mL, 15.28 mmol, 1.5 equiv) were combined and heated for 1 h at 90° C. (oil bath). After cooling to ambient temperature, the reaction was concentrated in vacuo and used as is. The crude 1-(dimethylamino)hepta-1,6-dien-3-one was taken up in EtOH (2 mL) and hydrazine (1.6 mL, 51.0 mmol, 5 equiv) was added. The mixture was then heated for 1 h at 90° C. (oil bath). After cooling to ambient temperature, the reaction was concentrated in vacuo. The crude product was purified by flash

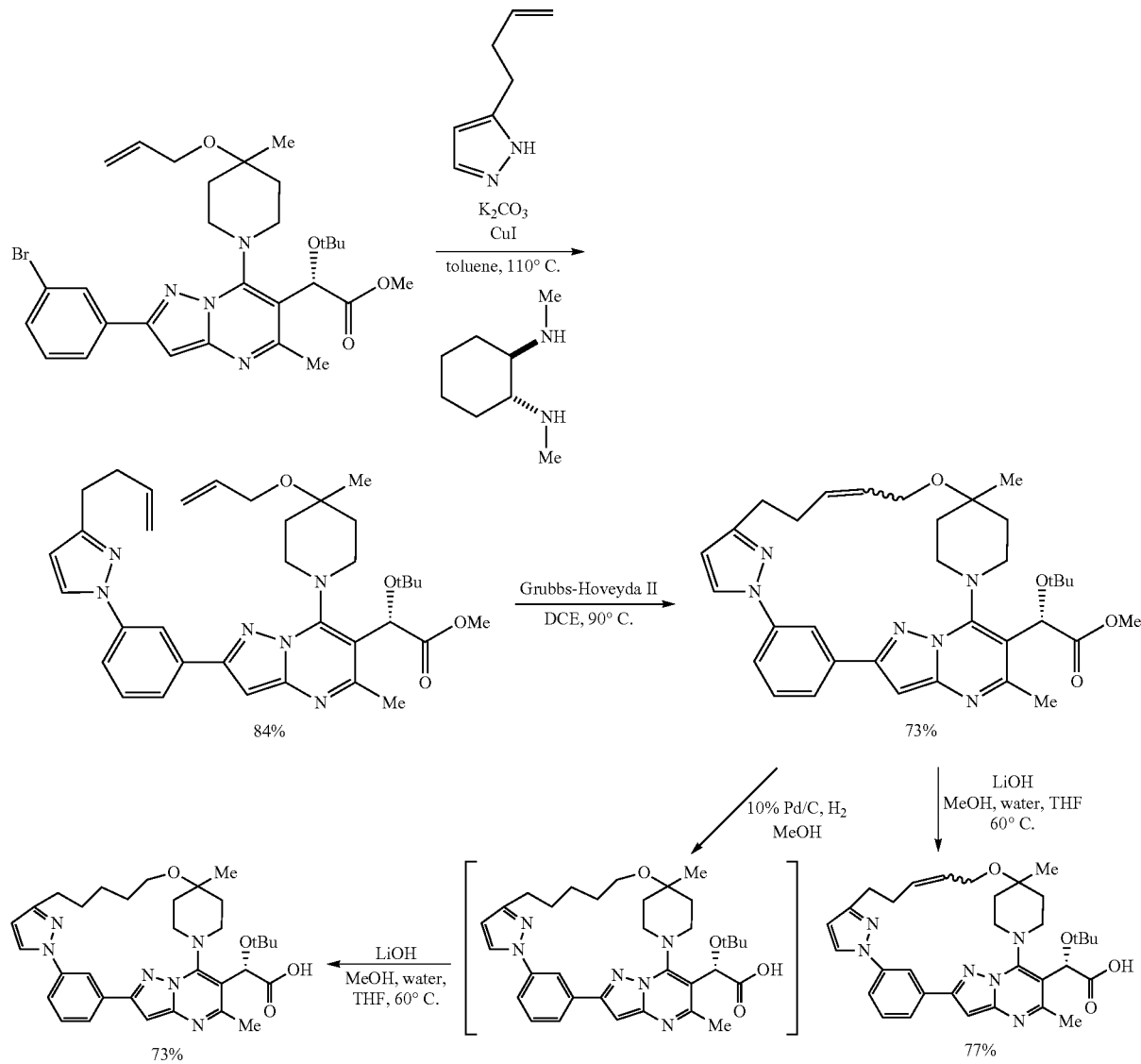

column chromatography (20-60% EtOAc in hexane) to provide the product (0.30 g, 24%). $^1$H NMR (400 MHz, CDCl$_3$) δ 7.50 (d, J=2.0 Hz, 1H), 6.12 (d, J=2.0 Hz, 1H), 5.89 (ddt, J=17.0, 10.4, 6.5 Hz, 1H), 5.14-4.99 (m, 2H), 2.80 (t, J=7.7 Hz, 2H), 2.48-2.40 (m, 2H); LCMS (ESI, M+1): 123.0.

Intermediate 14

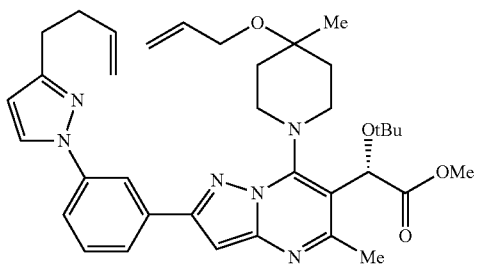 [SMILES: C=CCCc1ccn(-c2cccc(-c3cc4nc(C)c([C@H](OC(C)(C)C)C(=O)OC)c(N5CCC(C)(OCC=C)CC5)n4n3)c2)n1]

(S)-Methyl 2-(7-(4-(allyloxy)-4-methylpiperidin-1-yl)-2-(3-(3-(but-3-en-1-yl)-1H-pyrazol-1-yl)phenyl)-5-methylpyrazolo[1,5-a]pyrimidin-6-yl)-2-(tert-butoxy)acetate: To a solution of (S)-methyl 2-(7-(4-(allyloxy)-4-methylpiperidin-1-yl)-2-(3-bromophenyl)-5-methylpyrazolo[1,5-a]pyrimidin-6-yl)-2-(tert-butoxy)acetate (0.10 g, 0.171 mmol, 1 equiv) and 5-(but-3-en-1-yl)-1H-pyrazole (25 mg, 0.205 mmol, 1.2 equiv) in toluene (0.85 mL) was added (1R,2R)-N1,N2-dimethylcyclohexane-1,2-diamine (0.054 mL, 0.342 mmol, 2 equiv), CuI (33 mg, 0.171 mmol, 1 equiv), and K$_2$CO$_3$ (52 mg, 0.376 mmol, 2.2 equiv). Mixture was heated at 90° C. for 20 h. After cooling to ambient temperature, the reaction was concentrated in vacuo. The crude product was purified by flash column chromatography (0-30% EtOAc in hexane) to provide the product (0.09 g, 84%). $^1$H NMR (500 MHz, CDCl$_3$) δ 8.26 (br. s., 1H), 7.90 (d, J=2.5 Hz, 1H), 7.70 (dd, J=8.0, 0.9 Hz, 1H), 7.50 (t, J=7.9 Hz, 1H), 6.87 (s, 1H), 6.31 (d, J=2.4 Hz, 1H), 6.10-5.89 (m, 3H), 5.43 (d, J=17.2 Hz, 1H), 5.16 (d, J=10.1 Hz, 1H), 5.12 (dq, J=17.2, 1.7 Hz, 1H), 5.02 (dq, J=10.2, 1.4 Hz, 1H), 4.06-4.00 (m, 2H), 3.74 (s, 3H), 2.86 (dd, J=8.6, 6.9 Hz, 2H), 2.61 (s, 3H), 2.54-2.47 (m, 2H), 2.06-1.94 (m, 3H), 1.80-1.68 (m, 1H), 1.38 (br. s., 3H), 1.25 (s, 10H); LCMS (ESI, M+1): 627.4.

Intermediate 15

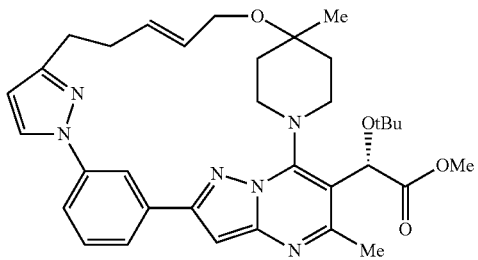 [SMILES: COC(=O)[C@@H](OC(C)(C)C)c1c(C)nc2cc3nn2c1N1CCC(C)(CC1)OC/C=C/CCc1ccn(n1)-c1cccc-3c1]

Methyl (2S)-tert-butoxy[(21E)-4,25-dimethyl-24-oxa-1,5,7,8,15,30-hexaazahexacyclo[23.2.2.1$^{6,9}$.1$^{10,14}$.1$^{15,18}$.0$^{2,7}$]dotriaconta-2,4,6(32),8,10(31),11,13,16,18(30),21-decaen-3-yl]acetate: A solution of (S)-methyl 2-(7-(4-(allyloxy)-4-methylpiperidin-1-yl)-2-(3-(3-(but-3-en-1-yl)-1H-pyrazol-1-yl)phenyl)-5-methylpyrazolo[1,5-a]pyrimidin-6-yl)-2- (tert-butoxy)acetate (0.080 g, 0.128 mmol, 1 equiv) in DCE (64 mL) was heated to 90° C. The Hoyveda Grubbs 2$^{nd}$ generation catalyst (16 mg, 0.026 mmol, 0.2 equiv) was added. The pale green brown solution was stirred for 2 h and then allowed to cool to ambient temperature. The reaction was concentrated in vacuo. The crude product was purified by flash column chromatography (0-100% EtOAc in hexane) to provide the product (0.055 g, 73%). LCMS (ESI, M+1): 599.4.

Example 1

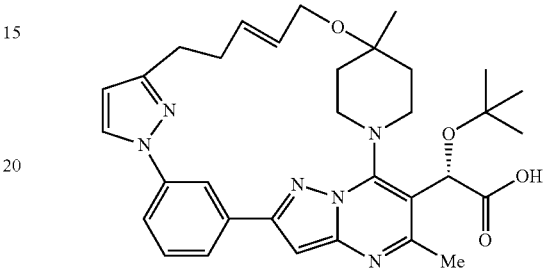

(2S)-tert-Butoxy[(21E)-4,25-dimethyl-24-oxa-1,5,7,8,15,30-hexaazahexacyclo[23.2.2.1$^{6,9}$.1$^{10,14}$.1$^{15,18}$.0$^{2,7}$]dotriaconta-2,4,6(32),8,10(31),11,13,16,18(30),21-decaen-3-yl]acetic acid: To a solution of methyl (2S)-tert-butoxy[(21E)-4,25-dimethyl-24-oxa-1,5,7,8,15,30-hexaazahexacyclo[23.2.2.1$^{6,9}$.1$^{10,14}$.1$^{15,18}$.0$^{2,7}$]dotriaconta-2,4,6(32),8,10(31),11,13,16,18(30),21-decaen-3-yl]acetate (20 mg, 0.033 mmol, 1 equiv) in MeOH (1 mL), THF (0.67 mL) and water (0.33 mL) was added LiOH.H$_2$O (100 mg, 2.4 mmol, 72 equiv). The reaction was heated to 60° C. for 2 h. Upon cooling to ambient temperature, the reaction was filtered and purified via preparative LC/MS with the following conditions: Column: Waters XBridge C18, 19×200 mm, 5-μm particles; Mobile Phase A: water with 20-mM ammonium acetate; Mobile Phase B: 95:5 acetonitrile:water with 20-mM ammonium acetate; Gradient: 40-80% B over 25 minutes, then a 5-minute hold at 100% B; Flow: 20 mL/min. Product (15 mg, 77%) isolated. $^1$H NMR (500 MHz, DMSO-d$_6$) δ 8.68 (s, 1H), 8.35 (d, J=2.1 Hz, 1H), 7.87 (d, J=7.9 Hz, 1H), 7.70 (d, J=7.6 Hz, 1H), 7.61-7.54 (m, 1H), 7.12 (s, 1H), 6.39 (d, J=2.1 Hz, 1H), 5.93 (br. s., 1H), 5.82 (br. s., 1H), 5.74 (br. s., 1H), 4.38 (br. s., 1H), 3.87 (br. s., 2H), 3.73 (br. s., 1H), 3.19 (br. s., 2H), 2.83 (t, J=11.6 Hz, 2H), 2.75-2.67 (m, 1H), 2.56 (s, 3H), 2.37-2.28 (m, 1H), 1.99 (br. s., 1H), 1.85 (br. s., 1H), 1.77 (br. s., 1H), 1.65-1.53 (m, 1H), 1.23 (s, 3H), 1.19 (s, 9H); LCMS (ESI, M): 584.3.

Example 2

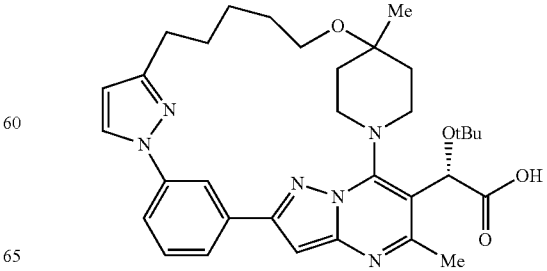

(2S)-tert-Butoxy[4,25-dimethyl-24-oxa-1,5,7,8,15,30-hexaazahexacyclo[23.2.2.1$^{6,9}$.1$^{10,14}$.1$^{15,18}$.0$^{2,7}$]dotriaconta-

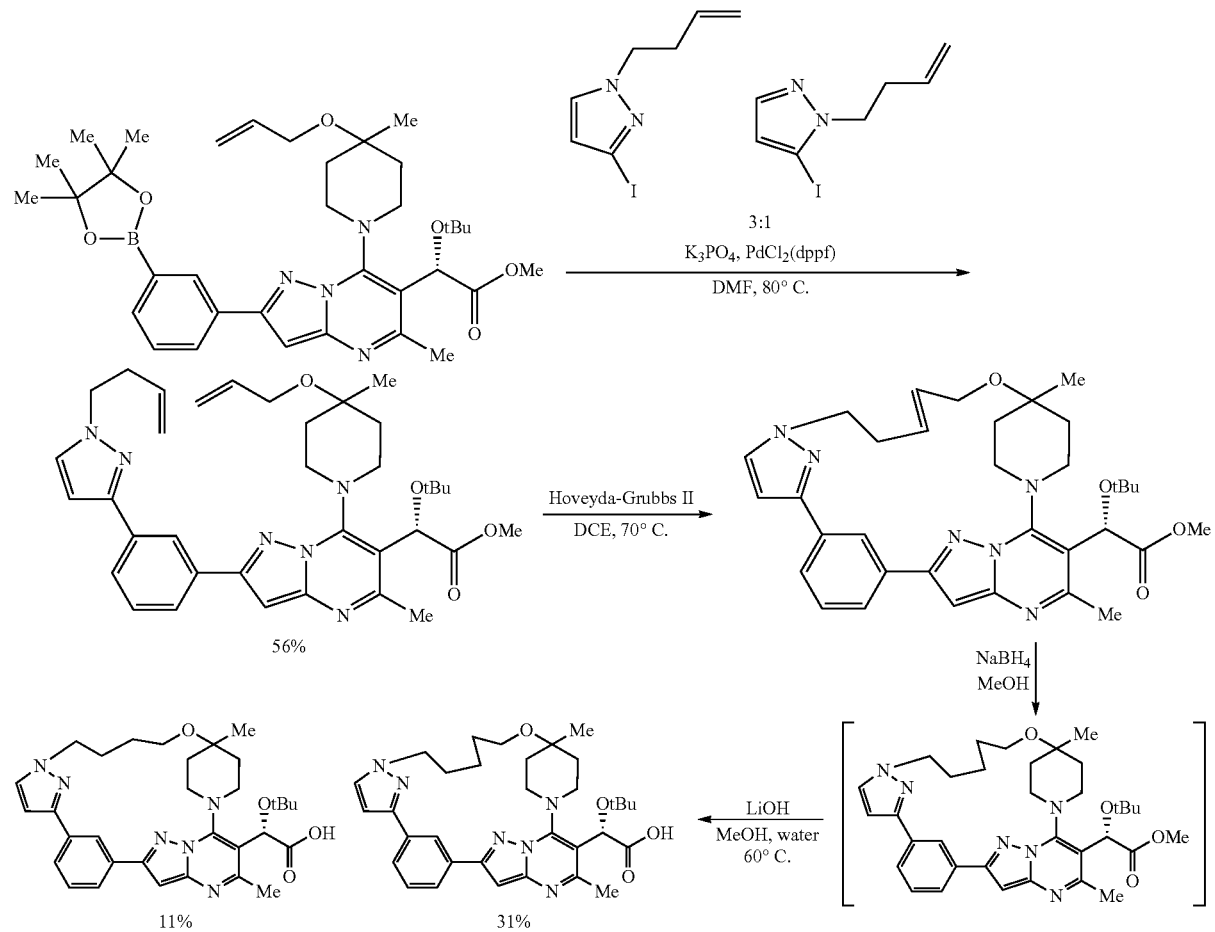

2,4,6(32),8,10(31),11,13,16,18(30)-nonaen-3-yl]acetic acid: A solution of methyl (2S)-tert-butoxy[(21E)-4,25-dimethyl-24-oxa-1,5,7,8,15,30-hexaazahexacyclo[23.2.2.1$^{6,9}$.1$^{10,14}$.1$^{15,18}$.0$^{2,7}$]dotriaconta-2,4,6(32),8,10(31),11,13,16,18(30),21-decaen-3-yl]acetate (35 mg, 0.058 mol, 1 equiv) and 10% Pd/C (6 mg, 0.006 mmol, 0.1 equiv) in MeOH was stirred under a balloon of hydrogen for 2 h. The mixture was filtered through a pad of Celite eluting with MeOH. The filtrate was then concentrated in vacuo to provide the crude hydrogenation product. This product was taken up in MeOH (1 mL), THF (0.67 mL) and water (0.33 mL) was added LiOH.H$_2$O (100 mg, 2.4 mmol, 41 equiv). The reaction was heated to 60° C. for 2 h. Upon cooling to ambient temperature, the reaction was filtered and purified via preparative LC/MS with the following conditions: Column: Waters XBridge C18, 19×200 mm, 5-μm particles; Mobile Phase A: water with 20-mM ammonium acetate; Mobile Phase B: 95:5 acetonitrile:water with 20-mM ammonium acetate; Gradient: 35-75% B over 20 minutes, then a 5-minute hold at 100% B; Flow: 20 mL/min. Product (25 mg, 73%) isolated. $^1$H NMR (500 MHz, DMSO-d$_6$) δ 8.70 (s, 1H), 8.35 (s, 1H), 7.84 (d, J=7.6 Hz, 1H), 7.69 (d, J=8.5 Hz, 1H), 7.58-7.51 (m, 1H), 7.10 (s, 1H), 6.35 (s, 1H), 5.69 (br. s., 1H), 4.31 (t, J=11.4 Hz, 1H), 3.76-3.66 (m, 2H), 3.28 (d, J=6.1 Hz, 3H), 2.71 (br. s., 2H), 2.53 (s, 3H), 1.82-1.60 (m, 5H), 1.58-1.32 (m, 5H), 1.20-1.13 (m, 12H); LCMS (ESI, M): 586.3.

Intermediate 16

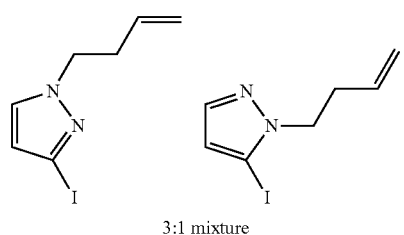

3:1 mixture 1-(But-3-en-1-yl)-3-iodo-1H-pyrazole. To a solution of 5-iodo-1H-pyrazole (1.34 g, 6.91 mmol, 1 equiv) in DMF (23 mL) was added 60% NaH (0.33 g, 8.29 mmol, 1.2 equiv). After 10 min, 4-bromobut-1-ene (0.84 mL, 8.29 mmol, 1.2 equiv) was added. After stirring 3 d, the reaction was added to water and extracted with EtOAc (×3). The combined EtOAc extracts were dried (Na$_2$SO$_4$) and concentrated in vacuo. The crude product was purified by flash column chromatography (0-100% EtOAc in hexane) to provide a 3:1 mixture of product isomers (1.12 g, 65%) as a colorless oil. Major isomer: 1H NMR (400 MHz, CDCl$_3$) δ 7.21 (d, J=2.3 Hz, 1H), 6.39 (d, J=2.3 Hz, 1H), 5.80-5.68

(m, 1H), 5.13-5.05 (m, 2H), 4.20 (t, J=7.2 Hz, 2H), 2.61 (qt, J=7.0, 1.3 Hz, 2H). Minor isomer: ¹H NMR (400 MHz, CDCl₃) 7.53 (d, J=1.8 Hz, 1H), 6.42 (d, J=1.8 Hz, 1H), 5.81 (ddt, J=17.1, 10.2, 6.9 Hz, 1H), 5.14-5.05 (m, 2H), 4.27 (t, J=7.3 Hz, 2H), 2.65-2.58 (m, 2H).

Intermediate 17

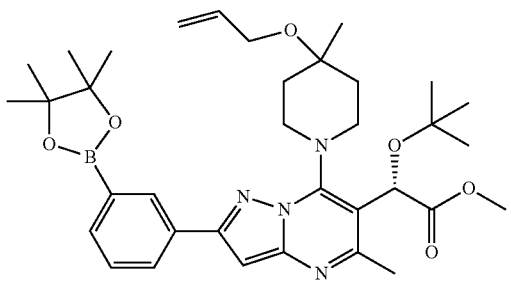

(S)-Methyl 2-(7-(4-(allyloxy)-4-methylpiperidin-1-yl)-5-methyl-2-(3-(4,4,5,5-tetramethyl-1,3,2-dioxaborolan-2-yl)phenyl)pyrazolo[1,5-a]pyrimidin-6-yl)-2-(tert-butoxy)acetate: A mixture of (S)-methyl 2-(7-(4-(allyloxy)-4-methylpiperidin-1-yl)-2-(3-bromophenyl)-5-methylpyrazolo[1,5-a]pyrimidin-6-yl)-2-(tert-butoxy)acetate (3 g, 5.12 mmol, 1 equiv), 4,4,4',4',5,5,5',5'-octamethyl-2,2'-bi(1,3,2-dioxaborolane) (1.952 g, 7.69 mmol, 1.5 equiv), KOAc (1.760 g, 17.93 mmol, 3.5 equiv) and Pd(dppf)Cl₂ (0.375 g, 0.512 mmol, 0.1 equiv) was flushed with N₂ for 1 min. Then, DMF (40 mL) was added and degassed for additional 1 min by bubbling N₂ through reaction mixture and then the resulting dark mixture was heated at 95-100° C. for 5 h. Upon cooling to ambient temperature, the reaction was diluted with water (5 mL) and extracted with EtOAc (3×15 mL). The EtOAc layers were washed with water (3×5 mL), brine (5 mL), dried (Na₂SO₄), and concentrated in vacuo. The crude product was purified by flash column chromatography (0-20% EtOAc/hexane) to obtain (S)-methyl 2-(7-(4-(allyloxy)-4-methylpiperidin-1-yl)-5-methyl-2-(3-(4,4,5,5-tetramethyl-1,3,2-dioxaborolan-2-yl)phenyl)pyrazolo[1,5-a]pyrimidin-6-yl)-2-(tert-butoxy)acetate (2.84 g, 75%) as a white solid. 1H NMR (400 MHz, CDCl₃) δ 8.39 (br. s., 1H), 8.20 (br. s., 1H), 7.84 (dt, J=7.3, 1.3 Hz, 1H), 7.47 (t, J=7.5 Hz, 1H), 6.88 (s, 1H), 6.17-5.86 (m, 2H), 5.47 (d, J=16.6 Hz, 1H), 5.24 (d, J=10.5 Hz, 1H), 4.50-2.50 (m, 4H), 4.05 (d, J=5.3 Hz, 2H), 3.75 (s, 3H), 2.62 (s, 3H), 2.09-1.91 (m, 2H), 1.76 (br. s., 1H), 1.65-1.60 (m, 1H), 1.40 (s, 12H), 1.29-1.24 (m, 12H). LCMS (ESI, M+1): 633.37.

Intermediate 18

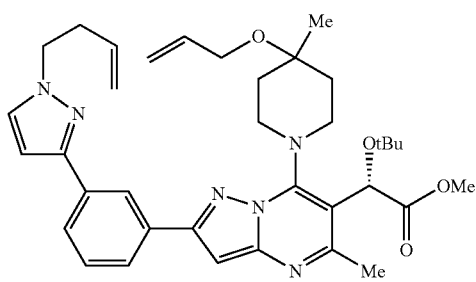 [SMILES: C=CCCn1ccc(-c2cccc(-c3cc4nc(C)c([C@H](OC(C)(C)C)C(=O)OC)c(N5CCC(C)(OCC=C)CC5)n4n3)c2)n1]

(S)-Methyl 2-(7-(4-(allyloxy)-4-methylpiperidin-1-yl)-2-(3-(1-(but-3-en-1-yl)-1H-pyrazol-3-yl)phenyl)-5-methylpyrazolo[1,5-a]pyrimidin-6-yl)-2-(tert-butoxy)acetate: A solution of (S)-methyl 2-(7-(4-(allyloxy)-4-methylpiperidin-1-yl)-5-methyl-2-(3-(4,4,5,5-tetramethyl-1,3,2-dioxaborolan-2-yl)phenyl)pyrazolo[1,5-a]pyrimidin-6-yl)-2-(tert-butoxy)acetate (40 mg, 0.063 mmol, 1 equiv), 1-(but-3-en-1-yl)-3-iodo-1H-pyrazole (25 mg of a 3:1 isomeric mixture from previous step, 0.10 mmol, 1.6 equiv), 1,1'-Bis(diphenylphosphino)ferrocenepalladium(II) dichloride (10 mg, 0.013 mmol, 0.2 mmol), and K₃PO₄ (0.095 mL of a 2 M aqueous solution, 0.19 mmol, 3 equiv) in DMF (0.6 mL) was heated at 80° C. (oil bath) for 3 h. Upon cooling to ambient temperature, the reaction was added to a saturated aqueous NaHCO₃ solution and extracted with EtOAc (×2). The combined EtOAc extracts were dried (Na₂SO₄) and concentrated in vacuo. The crude product was purified by flash column chromatography (10-100% EtOAc in hexane) to provide the product (22 mg, 56%) as a white foam. ¹H NMR (400 MHz, CDCl₃) δ 8.08 (d, J=7.8 Hz, 1H), 8.01 (s, 1H), 7.60 (dd, J=5.3, 1.8 Hz, 1H), 7.54 (td, J=7.7, 4.1 Hz, 1H), 7.46-7.38 (m, 1H), 7.35-7.28 (m, 1H), 6.85-6.80 (m, 1H), 6.41-6.33 (m, 1H), 6.08-5.92 (m, 2H), 5.79-5.66 (m, 1H), 5.41 (d, J=15.8 Hz, 1H), 5.14 (br. s., 1H), 5.06-4.98 (m, 1H), 4.74 (d, J=5.5 Hz, 2H), 4.24 (t, J=7.4 Hz, 1H), 4.01 (br. s., 2H), 3.75 (s, 3H), 2.62 (s, 3H), 2.00-1.93 (m, 2H), 1.71 (dd, J=6.4, 1.4 Hz, 2H), 1.36 (s, 3H), 1.26 (d, J=1.3 Hz, 9H); LCMS (ESI, M+1): 627.35.

Examples 3 and 4

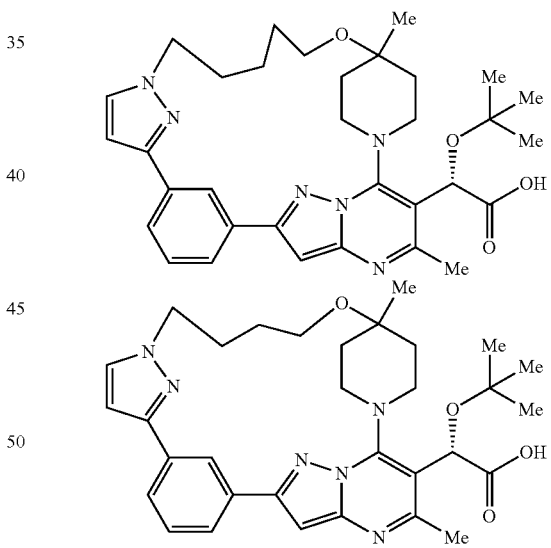

(2S)-tert-Butoxy[4,25-dimethyl-24-oxa-1,5,7,8,18,30-hexaazahexacyclo[23.2.2.1⁶,⁹.1¹⁰,¹⁴.1¹⁵,¹⁸.0²,⁷]dotriaconta-2,4,6(32),8,10(31),11,13,15(30),16-nonaen-3-yl]acetic acid and (2S)-tert-butoxy[4,24-dimethyl-23-oxa-1,5,7,8,18,29-hexaazahexacyclo[22.2.2.1⁶,⁹.1¹⁰,¹⁴.1¹⁵,¹⁸.0²,⁷]hentriaconta-2,4,6(31),8,10(30),11,13,15(29),16-nonaen-3-yl]acetic acid: A solution of (S)-methyl 2-(7-(4-(allyloxy)-4-methylpiperidin-1-yl)-2-(3-(1-(but-3-en-1-yl)-1H-pyrazol-3-yl)phenyl)-5-methylpyrazolo[1,5-a]pyrimidin-6-yl)-2-(tert-butoxy)acetate (0.022 g, 0.035 mmol, 1 equiv) in DCE (18 mL) was heated to 70° C. The Hoveyda Grubbs 2ⁿᵈ generation catalyst (2.2 mg, 0.0035 mmol, 0.1 equiv) was added. The pale green brown solution was stirred for 1 h at which time no reaction had occurred. The Grubbs 2nd generation catalyst (5 mg, 0.0059 mmol, 0.17 equiv) was added. After 4 h, the reaction was complete. Upon cooling to ambient temperature, the reaction was concentrated in vacuo. The dark residue was then taken up in MeOH (1 mL) and NaBH$_4$ (8 mg, 0.211 mmol, 6 equiv) was added. After stirring 1 h, the reaction was added to a saturated solution of NH$_4$Cl and extracted with DCM (×3). The DCM layer was dried (Na$_2$SO$_4$) and concentrated in vacuo. The crude product taken up in 9:1 MeOH:water (1 mL) and LiOH.H$_2$O (44 mg, 1.05 mmol, 30 equiv) was added. The reaction was heated to 60° C. for 1 h. Upon cooling to ambient temperature, the reaction was filtered and purified via preparative LC/MS with the following conditions: Column: Waters XBridge C18, 19×200 mm, 5-μm particles; Mobile Phase A: water with 20-mM ammonium acetate; Mobile Phase B: 95:5 methanol:water with 20-mM ammonium acetate; Gradient: 60-100% B over 40 minutes, then a 5-minute hold at 100% B; Flow: 20 mL/min the product (6.6 mg, 31%) and the minor byproduct (2.4 mg, 11%). Major isomer: $^1$H NMR (500 MHz, DMSO-d$_6$) δ 8.17 (s, 1H), 8.04 (d, J=7.9 Hz, 1H), 7.64-7.56 (m, 2H), 7.44 (d, J=7.6 Hz, 1H), 7.10 (s, 1H), 6.39 (d, J=1.8 Hz, 1H), 5.65 (s, 1H), 4.35 (br. s., 1H), 4.14-4.04 (m, 1H), 3.97 (s, 1H), 3.69-3.59 (m, 1H), 3.41 (d, J=4.9 Hz, 2H), 3.37-3.31 (m, 1H), 2.83-2.76 (m, 1H), 2.54 (s, 3H), 2.31-2.19 (m, 1H), 2.02 (br. s., 2H), 1.81-1.46 (m, 7H), 1.20 (s, 3H), 1.17 (s, 9H); LCMS (ESI, M): 586.3. Minor isomer: $^1$H NMR (500 MHz, DMSO-d$_6$) δ 8.40 (s, 1H), 8.05 (d, J=7.9 Hz, 1H), 7.61 (t, J=7.8 Hz, 1H), 7.55 (d, J=1.5 Hz, 1H), 7.48 (d, J=7.6 Hz, 1H), 7.14 (s, 1H), 6.43 (d, J=1.8 Hz, 1H), 5.86 (s, 1H), 4.58 (br. s., 1H), 4.06 (d, J=8.9 Hz, 2H), 3.78 (br. s., 1H), 3.46 (d, J=5.2 Hz, 2H), 3.13 (br. s., 1H), 2.60-2.57 (m, 1H), 2.56 (s, 3H), 1.84-1.77 (m, 8H), 1.24-1.16 (m, 12H); LCMS (ESI, M): 572.3.

Intermediate 19

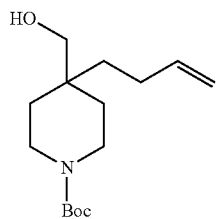 [SMILES: C=CCCC1(CO)CCN(C(=O)OC(C)(C)C)CC1]

tert-Butyl 4-(but-3-en-1-yl)-4-(hydroxymethyl)piperidine-1-carboxylate: To a solution of 1-tert-butyl 4-methyl 4-(but-3-en-1-yl)piperidine-1,4-dicarboxylate (21.2 g, 71.3 mmol) in THF (300 mL) at 0° C. was added 2M LAH/THF (35.6 mL, 71.3 mmol) and the resulting mixture was stirred at 0° C. for 1 h and then stirred at room temp for 2 h. The mixture was then recooled to 0° C. and water (2.7 mL), 1N NaOH (2.7 mL) and water (8.2 mL) were added successively and the mixture was stirred for 5 min. The solids were filtered off and the cake was washed with ethyl acetate. The filterate was washed with water (2×50 mL), brine (100 mL), dried (Na$_2$SO$_4$), filtered and concentrated under reduced pressure to give tert-butyl 4-(but-3-en-1-yl)-4-(hydroxymethyl)piperidine-1-carboxylate (16.5 g, 61.3 mmol, 86% yield) as yellow oil. $^1$H NMR (500 MHz, CDCl$_3$) δ 5.90-5.78 (m, 1H), 5.13-5.01 (m, 1H), 5.01-4.86 (m, 1H), 3.57-3.42 (m, 4H), 3.39-3.28 (m, 2H), 2.46-2.33 (m, 1H), 2.06-1.99 (m, 2H), 1.54-1.38 (m, 14H).

Intermediate 20

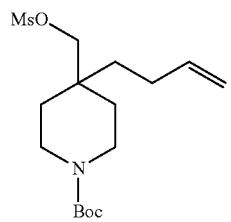

tert-Butyl 4-(but-3-en-1-yl)-4-(((methylsulfonyl)oxy)methyl)piperidine-1-carboxylate: Ms-Cl (5.59 mL, 71.7 mmol) was added dropwise at 0° C. to a stirred solution of tert-butyl 4-(but-3-en-1-yl)-4-(hydroxymethyl)piperidine-1-carboxylate (16.1 g, 59.8 mmol) TEA (16.66 mL, 120 mmol) and DMAP (0.365 g, 2.99 mmol) in CH$_2$Cl$_2$ (300 mL) and the mixture was stirred at room temp for 2 h. Water was then added and the mixture was extracted with methylene chloride (100 mL), dried (Na$_2$SO$_4$), filtered and concentrated. The residue was purified by Biotage (0-40% Hex/EtOAc) to afford tert-butyl 4-(but-3-en-1-yl)-4-(((methylsulfonyl)oxy)methyl)piperidine-1-carboxylate (18 g, 51.8 mmol, 87% yield) as colorless oil. $^1$H NMR (500 MHz, CDCl$_3$) δ 5.88-5.75 (m, 1H), 5.11-4.90 (m, 2H), 4.09 (s, 2H), 3.58-3.44 (m, 2H), 3.40-3.32 (m, 2H), 3.05 (s, 3H), 2.07-2.02 (m, 2H), 1.59-1.54 (m, 2H), 1.53-1.49 (m, 4H), 1.48 (s, 9H).

Intermediate 21

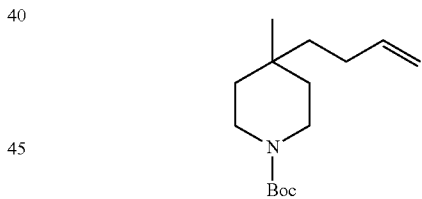

tert-Butyl 4-(but-3-en-1-yl)-4-methylpiperidine-1-carboxylate: To a solution of tert-butyl 4-(but-3-en-1-yl)-4-(((methylsulfonyl)oxy)methyl)piperidine-1-carboxylate (17 g, 48.9 mmol) in THF (250 mL) was added 1M solution of Superhydride (98 mL, 98 mmol) in THF and the resulting mixture was refluxed for 3 h. After cooling to room temp water was added and the mixture was extracted with ether (2×200 mL), washed with brine (100 mL), dried (Na$_2$SO$_4$), filtered and concentrated. The residue was purified by Biotage (0-20% EtOAc/hexane) to afford tert-butyl 4-(but-3-en-1-yl)-4-methylpiperidine-1-carboxylate (3.5 g, 13.81 mmol, 28.2% yield). $^1$H NMR (500 MHz, CDCl$_3$) δ 5.88-5.80 (m, 1H), 5.03 (dq, J=17.1, 1.7 Hz, 1H), 4.96 (ddt, J=10.2, 2.1, 1.1 Hz, 1H), 3.62-3.49 (m, 2H), 3.23 (ddd, J=13.4, 9.3, 3.8 Hz, 2H), 2.09-1.97 (m, 2H), 1.48 (s, 9H), 1.43-1.22 (m, 6H), 0.96 (s, 3H). LCMS (M+H)=254.2. 8 g of starting material was also recovered.

Intermediate 22

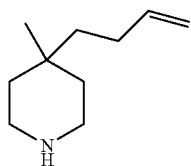

4-(But-3-en-1-yl)-4-methylpiperidine.HCl: A mixture of tert-butyl 4-(but-3-en-1-yl)-4-methylpiperidine-1-carboxylate (3.5 g, 13.81 mmol) and 4M HCl/dioxane (17.27 ml, 69.1 mmol) was stirred at room temp for 3 h. Mixture was then concentrated and dried under high vac to afford 4-(but-3-en-1-yl)-4-methylpiperidine.HCl (2.6 g, 13.70 mmol, 99% yield) as off-white solid. $^1$H NMR (500 MHz, DMSO-d$_6$) δ 5.83 (ddt, J=17.0, 10.3, 6.6 Hz, 1H), 5.05 (dq, J=17.1, 1.7 Hz, 1H), 5.00-4.80 (m, 1H), 3.11-2.90 (m, 5H), 2.05-1.90 (m, 2H), 1.56-1.42 (m, 5H), 1.38-1.26 (m, 2H), 0.95 (s,3H). LCMS (M+H)=154.1.

Intermediate 23

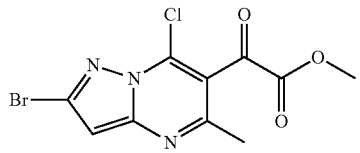 [SMILES: COC(=O)C(=O)c1c(C)nc2cc(Br)nn2c1Cl]

Methyl 2-(2-bromo-7-chloro-5-methylpyrazolo[1,5-a]pyrimidin-6-yl)-2-oxoacetate: To a solution of methyl 2-(2-bromo-7-chloro-5-methylpyrazolo [1,5-a]pyrimidin-6-yl)-2-hydroxyacetate (16.8 g, 50.2 mmol, 1 equiv, prepared as described in WO 2012033735) in DCM (250 mL) was added Dess-Martin periodinane (25.6 g, 60.2 mmol, 1.2 equiv). The reaction was stirred for 1 h. The reaction was diluted with DCM, washed with saturated aqueous NaHCO$_3$ (10 mL), dried (Na$_2$SO$_4$), and concentrated in vacuo. The crude product was purified by flash column chromatography (5-50% EtOAc/hexane) to provide the product (5.64 g, 34%) as a white solid. $^1$H NMR (500 MHz, CDCl$_3$) δ 6.77 (s, 1H), 3.99 (s, 3H), 2.60 (s, 3H); LCMS (ESI, M+1): 333.95.

Intermediate 24

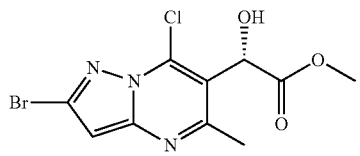 [SMILES: COC(=O)[C@@H](O)c1c(C)nc2cc(Br)nn2c1Cl]

(S)-Methyl 2-(2-bromo-7-chloro-5-methylpyrazolo[1,5-a]pyrimidin-6-yl)-2-hydroxyacetate: A solution of methyl 2-(2-bromo-7-chloro-5-methylpyrazolo[1,5-a]pyrimidin-6-yl)-2-oxoacetate (5.64 g, 16.96 mmol) and (R)-1-methyl-3,3-diphenylhexahydropyrrolo[1,2-c][1,3,2]oxazaborole (6.78 ml of a 1 M solution in toluene, 6.78 mmol, 0.4 equiv) in toluene (170 ml) was cooled to −40° C. (MeCN/CO$_2$). Catechoborane (5.7 mL of a 50% solution in toluene, 23.74 mmol, 1.4 equiv) was added over 10 min. After 1 h, the reaction was warmed was stirred at −15° C. and stirred for additional 1 h. The reaction was then diluted with EtOAc (30 mL), saturated aqueous Na$_2$CO$_3$ (10 mL) was added, and the reaction was removed from the cold bath. The biphasic mixture was stirred vigorously for 30 min. The organic phase was washed with saturated aqueous Na$_2$CO$_3$ (2×5 mL), dried (Na$_2$SO$_4$), and concentrated in vacuo. The crude product was purified by flash column chromatography (5-50% EtOAc/hexane) to afford the product (3.5 g, 62%) as off-white solid. $^1$H NMR (500 MHz, CDCl$_3$) δ 6.70 (s, 1H), 5.72 (d, J=2.1 Hz, 1H), 3.83 (s, 3H), 3.51 (d, J=2.7 Hz, 1H), 2.61 (s, 3H); LCMS (ESI, M+1): 335.20.

Intermediate 25

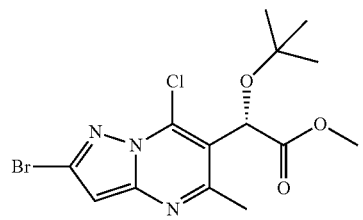 [SMILES: COC(=O)[C@@H](OC(C)(C)C)c1c(C)nc2cc(Br)nn2c1Cl]

(S)-Methyl 2-(2-bromo-7-chloro-5-methylpyrazolo[1,5-a]pyrimidin-6-yl)-2-(tert-butoxy)acetate: To a suspension of methyl 2-(2-bromo-7-chloro-5-methylpyrazolo[1,5-a]pyrimidin-6-yl)-2-hydroxyacetate (80 mg, 0.239 mmol, 1 equiv) in t-BuOAc (2 mL) and DCM (2 mL) was added 70% HClO$_4$ (0.022 mL, 0.359 mmol, 1.5 equiv). After stirring 4 h, the reaction was diluted with EtOAc, washed with water, saturated aqueous NaHCO$_3$, dried (Na$_2$SO$_4$), and concentrated in vacuo. The crude product was purified by flash column chromatography to give the product (56 mg, 60%). $^1$H NMR (500 MHz, MeOD) δ 6.75 (1H, s), 5.75 (1H, s), 3.74 (3H, s), 2.62 (3H, s), 1.27 (9H, s); LCMS (ESI, M+1): 391.97.

Intermediate 26

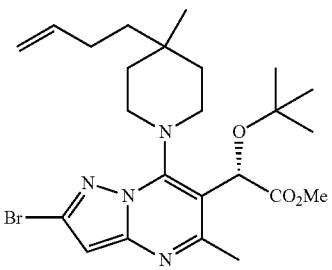 [SMILES: C=CCCC1(C)CCN(c2c([C@H](OC(C)(C)C)C(=O)OC)c(C)nc3cc(Br)nn23)CC1]

(S)-Methyl 2-(2-bromo-7-(4-(but-3-en-1-yl)-4-methylpiperidin-1-yl)-5-methylpyrazolo[1,5-a]pyrimidin-6-yl)-2-(tert-butoxy)acetate: A solution of 4-(but-3-en-1-yl)-4-methylpiperidine hydrochloride (471 mg, 2.483 mmol, 1.1 equiv), (S)-methyl 2-(2-bromo-7-chloro-5-methylpyrazolo[1,5-a]pyrimidin-6-yl)-2-(tert-butoxy)acetate (882 mg, 2.257 mmol, 1 equiv) and Hunig's Base (1.2 mL, 6.77 mmol, 3 equiv) in DMF (11 mL) was stirred at 65° C. (oil bath) for 2 h. Upon cooling to ambient temperature, the reaction was diluted with EtOAc, washed with saturated aqueous NaHCO₃, brine, dried (MgSO₄) and concentrated in vacuo. The crude product was purified by flash column chromatography (20% EtOAc/hexane) to give (S)-methyl 2-(2-bromo-7-(4-(but-3-en-1-yl)-4-methylpiperidin-1-yl)-5-methylpyrazolo[1,5-a]pyrimidin-6-yl)-2-(tert-butoxy)acetate (1.1 g, 96%). LCMS (ESI, M+1): 507.3.

equiv) in THF (55.5 ml) at 0° C. (ice/water). The resulting mixture was stirred vigorously for 10 min and then cooled to −30° C. (CO₂/acetone). n-BuLi (4.99 ml of a 1.6 M solution in hexane, 7.99 mmol, 1 equiv) was added and stirred for 15 mins. The mixture turned yellow clear. 3-Bromoprop-1-ene (1.014 ml, 11.99 mmol, 1.5 equiv) was added and stirred at −20° C. for 1 h. The reaction was quenched

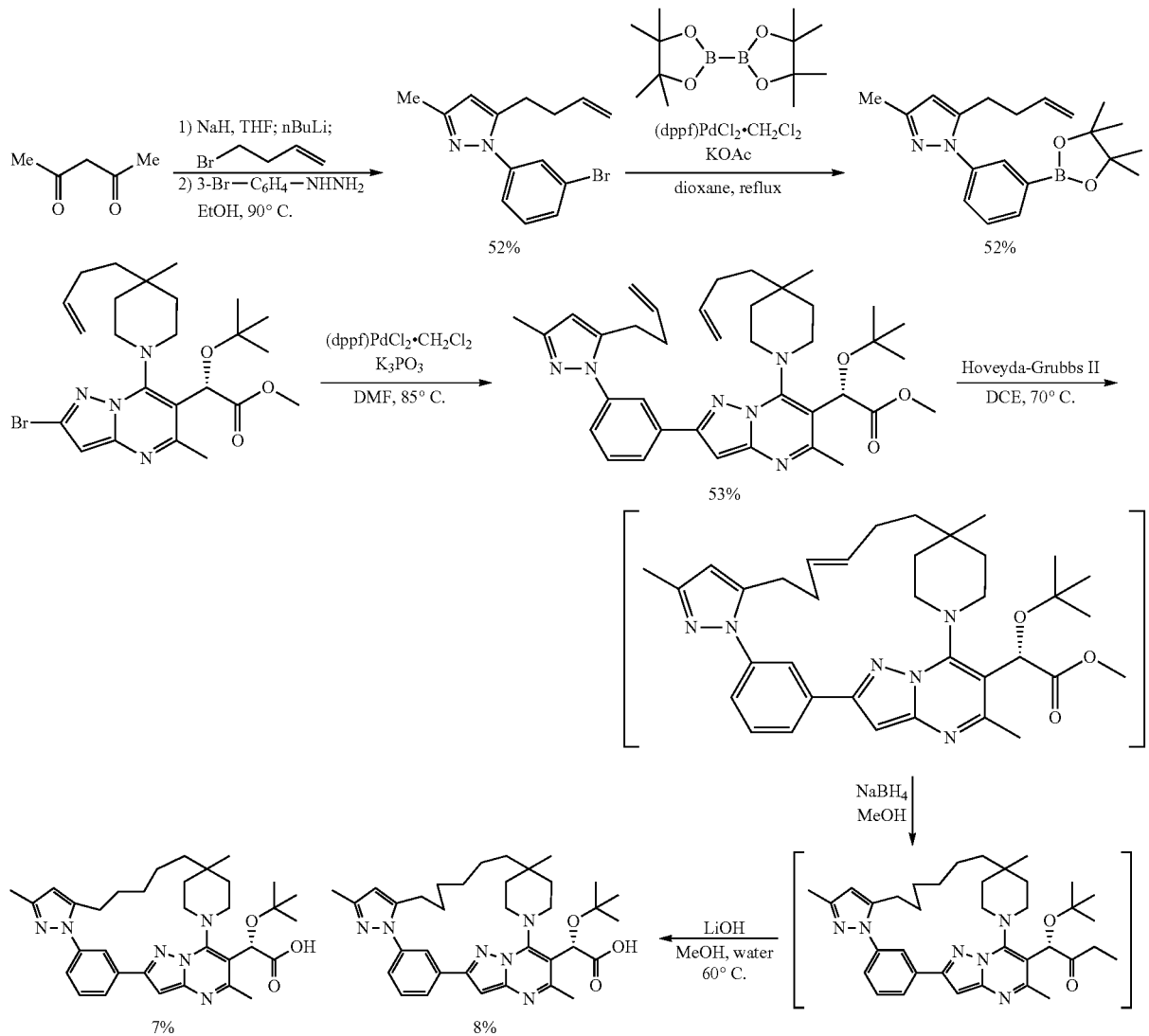

Intermediate 27

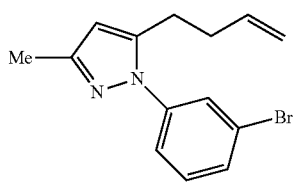 [SMILES: C=CCCc1cc(C)nn1-c1cccc(Br)c1]

1-(3-Bromophenyl)-5-(but-3-en-1-yl)-3-methyl-1H-pyrazole: Pentane-2,4-dione (1.03 ml, 9.99 mmol, 1.25 equiv) was added to a slurry of 60% NaH (0.48 g, 11.99 mmol, 1.5 with saturated aqueous NH₄Cl and extracted with ether (×2). The combined ether extracts were dried (MgSO₄) and concentrated in vacuo. The crude dione was dissolved in ethanol (5 ml) and (3-bromophenyl)hydrazine hydrochloride (2.2 g, 9.99 mmol) was added. The reaction was heated at 900 for 1 h. Upon cooling to ambient temperature, the reaction was concentrated in vacuo. The residue was added to a saturated aqueous solution of NaHCO₃ and extracted with EtOAc (×2). The combined EtOAc extracts were dried (Na₂SO₄) and concentrated in vacuo. The crude product was purified by flash column chromatography (0-10% EtOAc in hexane) to provide the product (1.5 g, 52%) and the other isomer (0.45 g, 15%). Isomer assignments confirmed by nOe. 1H NMR (400 MHz, CDCl₃) δ 7.63 (t, J=1.8 Hz, 1H), 7.50 (dt, J=7.7, 1.7 Hz, 1H), 7.41-7.32 (m, 2H), 6.05 (s, 1H), 5.80

(ddt, J=17.0, 10.4, 6.5 Hz, 1H), 5.08-5.00 (m, 2H), 2.77-2.70 (m, 2H), 2.40-2.34 (m, 2H), 2.31 (s, 3H).

Intermediate 28

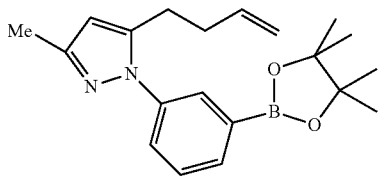 [SMILES: C=CCCc1cc(C)nn1-c1cccc(B2OC(C)(C)C(C)(C)O2)c1]

5-(But-3-en-1-yl)-3-methyl-1-(3-(4,4,5,5-tetramethyl-1,3,2-dioxaborolan-2-yl)phenyl)-1H-pyrazole: To a solution of 1-(3-bromophenyl)-5-(but-3-en-1-yl)-3-methyl-1H-pyrazole (500 mg, 1.717 mmol, 1 equiv), 4,4,4',4',5,5,5',5'-octamethyl-2,2'-bi(1,3,2-dioxaborolane) (458 mg, 1.803 mmol, 1.05 equiv), and KOAc (337 mg, 3.43 mmol, 2 equiv) in 1,4-dioxane (6.8 mL) was added (dppf)PdCl$_2$.CH$_2$Cl$_2$ (70 mg, 0.086 mmol, 0.05 equiv). The mixture was heated to reflux under nitrogen for 2 h. Upon cooling to ambient temperature, the reaction was diluted with water (50 mL) and EtOAc (50 mL) and filtered through Celite. The aqueous phase was further extracted with EtOAc (2×50 mL). The combined EtOAc extracts were washed with brine, dried (Na$_2$SO$_4$) and concentrated in vacuo. The crude product was purified by flash column chromatography (0-25% EtOAc in hexane) to provide the product (0.30 g, 52%) as pale yellow oil. LCMS (ESI, M+1): 339.25.

Intermediate 29

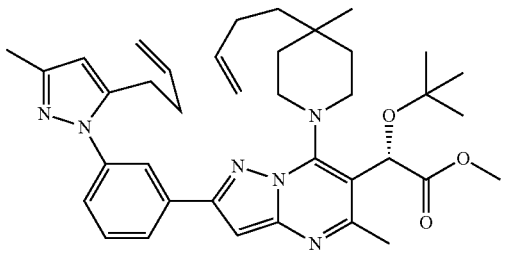

(S)-Methyl 2-(2-(3-(5-(but-3-en-1-yl)-3-methyl-H-pyrazol-1-yl)phenyl)-7-(4-(but-3-en-1-yl)-4-methylpiperidin-1-yl)-5-methylpyrazolo[1,5-a]pyrimidin-6-yl)-2-(tert-butoxy) acetate: The reaction mixture from 95165-091 was used without purification. to this solution was added 5-(but-3-en-1-yl)-3-methyl-1-(3-(4,4,5,5-tetramethyl-1,3,2-dioxaborolan-2-yl)phenyl)-1H-pyrazole (220 mg, 0.650 mmol), PdCl$_2$ (dppf)-CH$_2$Cl$_2$ adduct (48.3 mg, 0.059 mmol) and Phosphoric acid, potassium salt (1035 µl, 2.069 mmol). The mixture was stirred at 85° C. for half hour. The product purified by column with 0-100% EA/Hex to afford (S)-methyl 2-(2-(3-(5-(but-3-en-1-yl)-3-methyl-1H-pyrazol-1-yl)phenyl)-7-(4-(but-3-en-1-yl)-4-methylpiperidin-1-yl)-5-methylpyrazolo[1,5-a]pyrimidin-6-yl)-2-(tert-butoxy) acetate (200 mg, 0.313 mmol, 53.0% yield). LCMS (ESI, M+1): 639.4.

Example 5 and 6

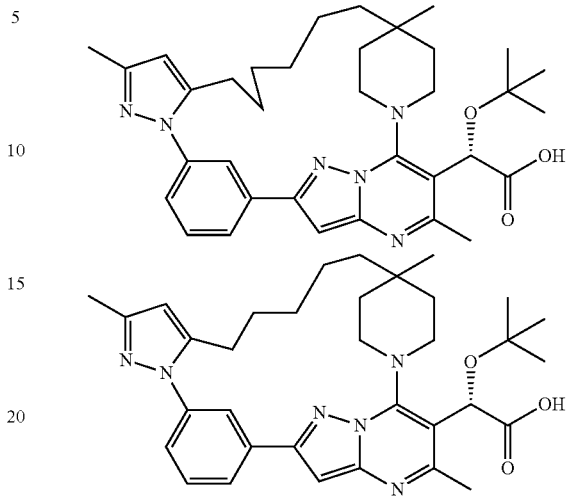

(2S)-tert-Butoxy[4,17,26-trimethyl-1,5,7,8,15,16-hexaazahexacyclo[24.2.2.1$^{6,9}$.1$^{10,14}$.0$^{2,7}$.0$^{15,19}$]dotriaconta-2,4,6(32),8,10(31),11,13,16,18-nonaen-3-yl]acetic acid and (2S)-tert-butoxy[4,17,25-trimethyl-1,5,7,8,15,16-hexaazahexacyclo[23.2.2.1$^{6,9}$.1$^{10,14}$.0$^{2,7}$.0$^{15,19}$]hentriaconta-2,4,6(31),8,10(30),11,13,16,18-nonaen-3-yl]acetic acid: To a solution of (S)-methyl 2-(2-(3-(5-(but-3-en-1-yl)-3-methyl-1H-pyrazol-1-yl)phenyl)-7-(4-(but-3-en-1-yl)-4-methylpiperidin-1-yl)-5-methylpyrazolo[1,5-a]pyrimidin-6-yl)-2-(tert-butoxy)acetate (80 mg, 0.125 mmol, 1 equiv) in DCE (63 mL) was added the Hoveyda Grubbs 2$^{nd}$ generation catalyst (16 mg, 0.025 mmol, 0.2 equiv). The reaction was heated for 4 h and then allowed to cool to ambient temperature. The desired product was the major product, but there was also significant amount of the one-carbon shortened homologue. The reaction was concentrated in vacuo and used as is without further purification. LCMS (ESI,M+1): 611.4. The residue was dissolved in MeOH (4.4 mL). To this solution was added NaBH$_4$ (30 mg, 0.786 mmol, 6 equiv) and stirred for 3 hours. The reaction was then added to saturated aqueous NaHCO$_3$ and extracted with EtOAc (×2). The combined EtOAc extracts were dried (Na$_2$SO$_4$) and concentrated in vacuo. The resulting residue was dissolved in MeOH (1.5 mL), THF (1.0 mL), and water (0.5 mL). and LiOH.H$_2$O (63 mg, 2.62 mmol, 20 equiv) was added. The reaction was heated to 60° C. for 2 h. Upon cooling to ambient temperature, the reaction was filtered and purified via preparative LC/MS with the following conditions: Column: XBridge C18, 19×mm, 5-µm particles; Mobile Phase A: 5:95 acetonitrile: water with 10-mM ammonium acetate; Mobile Phase B: 95:5 acetonitrile: water with 10-mM ammonium acetate; Gradient: 40-80% B over 20 minutes, then a 5-minute hold at 100% B; Flow: 20 mL/min. Two products isolated: the expected product (18.5 mg, 8%) and the one carbon shorter homologue (14.5 mg, 7%). Major isomer: $^1$H NMR (500 MHz, DMSO-d$_6$) δ 8.00 (d, J=7.3 Hz, 1H), 7.91 (br. s., 1H), 7.62 (t, J=7.8 Hz, 1H), 7.41 (d, J=7.3 Hz, 1H), 7.08 (s, 1H), 6.13 (s, 1H), 5.74 (s, 1H), 4.33 (t, J=11.9 Hz, 1H), 3.62 (t, J=11.6 Hz, 1H), 3.27 (d, J=8.9 Hz, 1H), 2.80-2.73 (m, 1H), 2.53 (s, 3H), 2.19 (s, 3H), 1.83-1.20 (m, 16H), 1.17 (s, 9H), 0.92 (s, 3H); LCMS (ESI, M): 598.4. Minor isomer: 1H NMR (500 MHz, DMSO-d$_6$) δ 8.15 (br.

s., 1H), 8.01 (d, J=7.3 Hz, 1H), 7.64 (t, J=7.9 Hz, 1H), 7.49 (d, J=7.3 Hz, 1H), 7.13 (s, 1H), 6.10 (s, 1H), 5.82 (br. s., 1H), 4.36 (br. s., 1H), 3.78 (br. s., 2H), 3.14 (br. s., 2H), 2.75-2.63 (m, 2H), 2.58 (br. s., 1H), 2.54 (br. s., 3H), 2.21 (s, 3H), 1.83-1.29 (m, 10H), 1.18 (s, 9H), 0.93 (br. s., 3H); LCMS (ESI, M): 584.3.
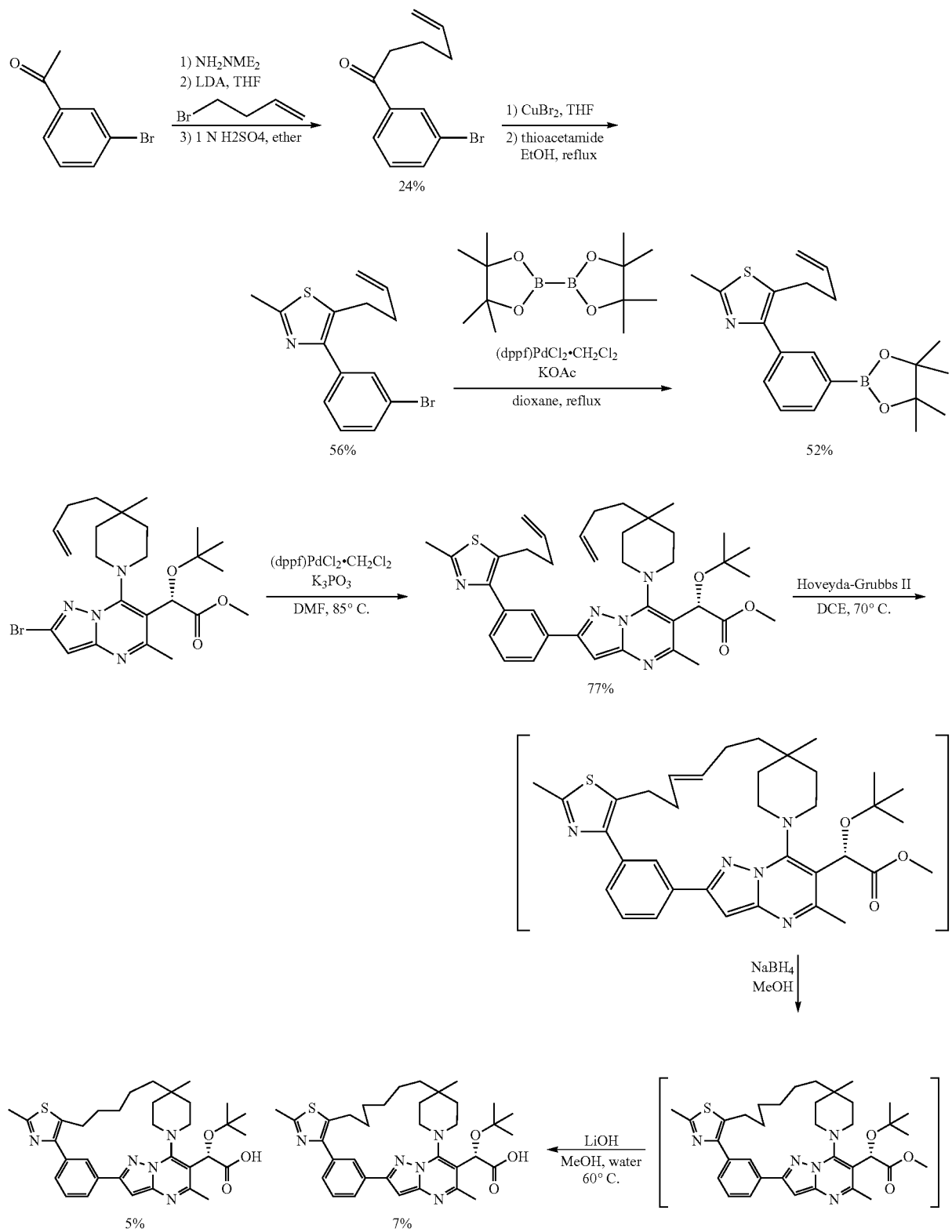

Intermediate 30

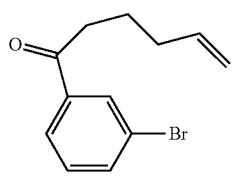

1-(3-Bromophenyl)hex-5-en-1-one. A solution of 1-(3-bromophenyl)ethanone (3.3 g, 16.98 mmol, 1 equiv), 1,1-dimethylhydrazine (4.98 g, 83 mmol, 5 equiv), and 3 Å molecular sieves in toluene (50 mL) was heated to reflux for 18 h. Upon cooling to ambient temperature, the solution was filtered. The filtrate was diluted with ether and washed with water. The ether layer was then dried (MgSO$_4$) and concentrated in vacuo to provide (E)-2-(1-(3-bromophenyl)ethyl-idene)-1,1-dimethylhydrazine (3.29 g, 82%) as a yellow oil. To a solution of (E)-2-(1-(3-bromophenyl)ethylidene)-1,1-dimethylhydrazine (0.60 g, 2.49 mmol, 1 equiv) in THF (12.4 mL) at 0° C. (ice/water) was added LDA (1.5 mL of a 2 M solution in THF, 2.99 mmol, 1.2 equiv). After 1 h, 4-bromo-1-butene (0.30 mL, 2.99 mmol, 1.2 equiv) was added and the reaction was allowed to warm to ambient temperature. After stirring 1 h, the reaction was added to water and extracted with ether (×2). The combined ether extracts were dried (MgSO$_4$) and concentrated in vacuo. The crude alkylation product was taken up in ether (30 mL) and treated with 1 N H$_2$SO$_4$ (10 mL). After 2 h, the ether layer was separated and washed with saturated aqueous NaHCO$_3$. The ether layer was dried (MgSO$_4$) and concentrated in vacuo. The crude product was purified by flash column chromatography (0-60% DCM in hexane) to provide the product (0.22 g, 24%). $^1$H NMR (400 MHz, CDCl$_3$) δ 8.12-8.06 (m, 1H), 7.92-7.86 (m, 1H), 7.74-7.65 (m, 1H), 7.40-7.32 (m, 1H), 5.83 (ddt, J=17.1, 10.3, 6.7 Hz, 1H), 5.10-4.98 (m, 2H), 3.01-2.89 (m, 2H), 2.23-2.12 (m, 2H), 1.93-1.80 (m, 2H).

Intermediate 31

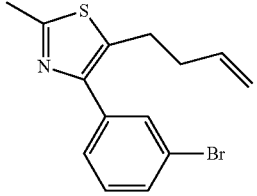 [SMILES: C=CCCc1sc(C)nc1-c1cccc(Br)c1]

4-(3-Bromophenyl)-5-(but-3-en-1-yl)-2-methylthiazole: To a solution of 1-(3-bromophenyl)hex-5-en-1-one (0.22 g, 0.869 mmol, 1 equiv) in THF (8.7 mL) was added CuBr$_2$ (0.43 g, 1.912 mmol, 2.2 equiv). After stirring 3 h, the reaction was diluted with ether and filtered. Ether filtrate washed with 1 N NaS$_2$O$_3$, dried (MgSO$_4$), and concentrated in vacuo. The crude bromide was taken up in EtOH (9 mL) and thioacetamide (0.26 g, 3.48 mmol, 4 equiv) was added. The reaction was heated to reflux for 18 h. After cooling to ambient temperature, the reaction was added to saturated aqueous NaHCO$_3$ and extracted with DCM (×2). The combined DCM layers were dried (Na$_2$SO$_4$) and concentrated in vacuo. The crude product was purified by flash column chromatography (0-100% DCM in hexane) to provide the product (0.15 g, 56%). $^1$H NMR (400 MHz, CDCl$_3$) δ 7.77 (t, J=1.8 Hz, 1H), 7.52-7.46 (m, 2H), 7.32-7.28 (m, 1H), 5.83 (dd, J=17.1, 10.3 Hz, 1H), 5.12-5.02 (m, 2H), 3.03-2.94 (m, 2H), 2.70 (s, 3H), 2.47-2.37 (m, 2H); LCMS (ESI, M+1): 308.0.

Intermediate 32

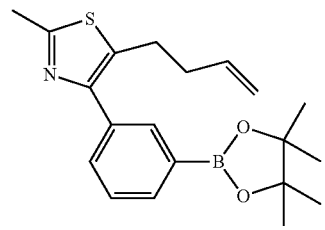

5-(But-3-en-1-yl)-2-methyl-4-(3-(4,4,5, 5-tetramethyl-1, 3,2-dioxaborolan-2-yl)phenyl)thiazole: A solution of 4-(3-bromophenyl)-5-(but-3-en-1-yl)-2-methylthiazole (140 mg, 0.454 mmol, 1 equiv), 4,4,4',4',5,5,5',5'-octamethyl-2,2'-bi(1, 3,2-dioxaborolane) (173 mg, 0.681 mmol), KOAc (89 mg, 0.908 mmol) and (dppf)PdCl$_2$.CH$_2$Cl$_2$ (37 mg, 0.045 mmol, 0.1 equiv) in 1,4-dioxane (1.8 mL) was heated to reflux for 2 h. Upon cooling to ambient temperature, the reaction was diluted with water (50 mL) and EtOAc (50 mL) and filtered through Celite. The aqueous phase was further extracted with EtOAc (2×50 mL). The combined EtOAc extracts were washed with brine, dried (Na$_2$SO$_4$), and concentrated in vacuo. The crude product was purified by flash column chromatography (0-30% EtOAc in hexane) to provide the product (84 mg, 52%) as pale yellow oil. LCMS (ESI, M+1): 356.2.

Intermediate 33

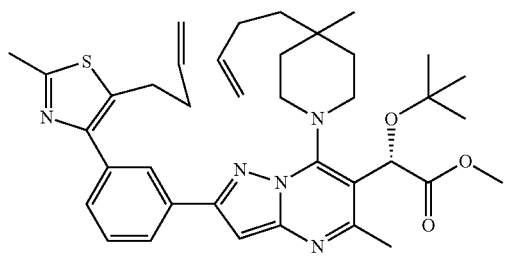

(S)-Methyl 2-(2-(3-(5-(but-3-en-1-yl)-2-methylthiazol-4-yl)phenyl)-7-(4-(but-3-en-1-yl)-4-methylpiperidin-1-yl)-5-methylpyrazolo[1,5-a]pyrimidin-6-yl)-2-(tert-butoxy)acetate: A solution of 5-(but-3-en-1-yl)-2-methyl-4-(3-(4,4,5, 5-tetramethyl-1,3,2-dioxaborolan-2-yl)phenyl)thiazole (84.0 mg, 0.236 mmol, 1.2 equiv), (S)-methyl 2-(2-bromo-7-(4-(but-3-en-1-yl)-4-methylpiperidin-1-yl)-5-methylpyrazolo [1,5-a]pyrimidin-6-yl)-2-(tert-butoxy)acetate (100 mg, 0.197 mmol, 1 equiv), PdCl$_2$(dppf)-CH$_2$Cl$_2$ adduct (16.1 mg, 0.02 mmol, 0.1 equiv), and K$_3$PO$_4$ (0.49 mL of a 2 N aqueous solution, 0.985 mmol, 5 equiv) in DMF (2 mL) was heated at 85° C. for 30 min. Upon cooling to ambient temperature, the mixture was loaded onto a silica gel column and purified by flash column chromatography (0-100% EtOAc in hexane) to provide the product (100 mg, 77%). LCMS (ESI, M+1): 656.4.

Examples 7 and 8

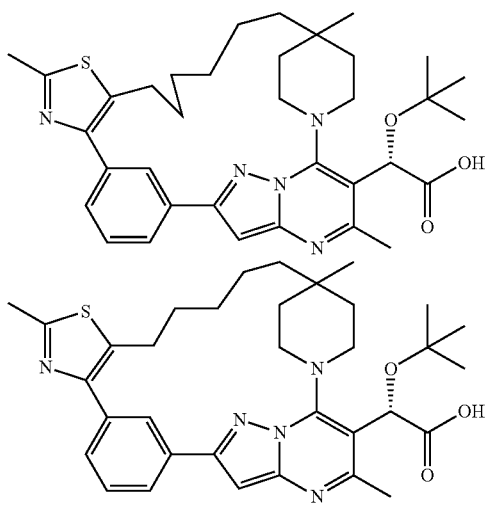

(2S)-tert-Butoxy[4,17,26-trimethyl-18-thia-1,5,7,8,16-pentaazahexacyclo[24.2.2.1$^{6,9}$.1$^{10,14}$.0$^{2,7}$.0$^{15,19}$]dotriaconta-2,4,6(32),8,10(31),11,13,15(19),16-nonaen-3-yl]acetic acid and (2S)-tert-butoxy[4,17,25-trimethyl-18-thia-1,5,7,8,16-pentaazahexacyclo[23.2.2.1$^{6,9}$.1$^{10,14}$.0$^{2,7}$.0$^{15,19}$]hentriaconta-2,4,6(31),8,10(30),11,13,15(19),16-nonaen-3-yl]acetic acid: TS)-methyl 2-(2-(3-(5-(but-3-en-1-yl)-2-methylthiazol-4-yl)phenyl)-7-(4-(but-3-en-1-yl)-4-methylpiperidin-1-yl)-5-methylpyrazolo[1,5-a]pyrimidin-6-yl)-2-(tert-butoxy)acetate (100 mg, 0.152 mmol, 1 equiv) in DCE (76 mL) was added the Hoveyda Grubbs 2$^{nd}$ generation catalyst (19 mg, 0.030 mmol, 0.2 equiv). The reaction was heated for 6 h and then allowed to cool to ambient temperature. The desired product was the major product, but there was also significant amount of the one-carbon shortened homologue. The reaction was concentrated in vacuo and used as is without further purification. LCMS (ESI, M+1): 628.3. The residue was dissolved in MeOH (4.4 mL). To this solution was added NaBH$_4$ (30 mg, 0.786 mmol, 5 equiv) and stirred for 3 hours. The reaction was then added to saturated aqueous NaHCO$_3$ and extracted with EtOAc (×2). The combined EtOAc extracts were dried (Na$_2$SO$_4$) and concentrated in vacuo. The resulting residue was dissolved in MeOH (1.5 mL), THF (1.0 mL), and water (0.5 mL). and LiOH.H$_2$O (63 mg, 2.62 mmol, 17 equiv) was added. The reaction was heated to 60° C. for 2 h. Upon cooling to ambient temperature, the reaction was filtered and purified via preparative LC/MS with the following conditions: Column: Waters XBridge C18, 19×200 mm, 5-μm particles; Mobile Phase A: water with 20-mM ammonium acetate; Mobile Phase B: 95:5 acetonitrile:water with 20-mM ammonium acetate; Gradient: 50-90% B over 20 minutes, then a 5-minute hold at 100% B; Flow: 20 mL/min. Two products isolated: the expected product (5.7 mg, 7%) and the one carbon shorter homologue (3.9 mg, 5%). $^1$H NMR (500 MHz, DMSO-d$_6$) δ 8.09 (s, 1H), 7.96 (d, J=5.2 Hz, 1H), 7.59-7.52 (m, 2H), 7.07 (s, 1H), 5.69 (s, 1H), 4.34 (br. s., 1H), 3.58 (d, J=11.3 Hz, 1H), 2.88-2.79 (m, 3H), 2.64 (s, 3H), 2.52 (br. s., 3H), 1.88-1.22 (m, 15H), 1.17 (s, 9H), 0.94 (s, 3H); LCMS (ESI, M): 615.3. $^1$H NMR (500 MHz, DMSO-d$_6$) δ 8.29 (s, 1H), 7.98 (d, J=7.6 Hz, 1H), 7.65 (d, J=7.3 Hz, 1H), 7.60-7.54 (m, 1H), 7.13 (s, 1H), 5.86 (s, 1H), 4.43-4.33 (m, 1H), 3.75 (d, J=11.3 Hz, 1H), 3.13 (br. s., 1H), 2.85 (t, J=7.0 Hz, 1H), 2.67 (br. s., 1H), 2.64 (s, 3H), 2.54 (s, 3H), 1.96-1.36 (m, 13H), 1.18 (s, 9H), 0.92 (s, 3H); LCMS (ESI, M): 601.3.

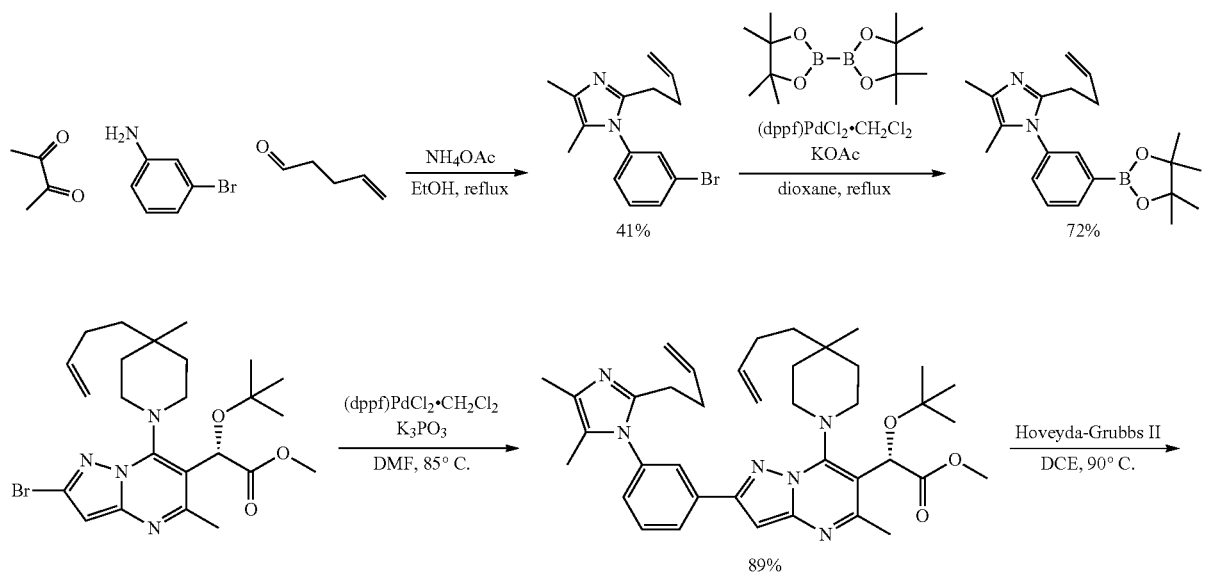

-continued

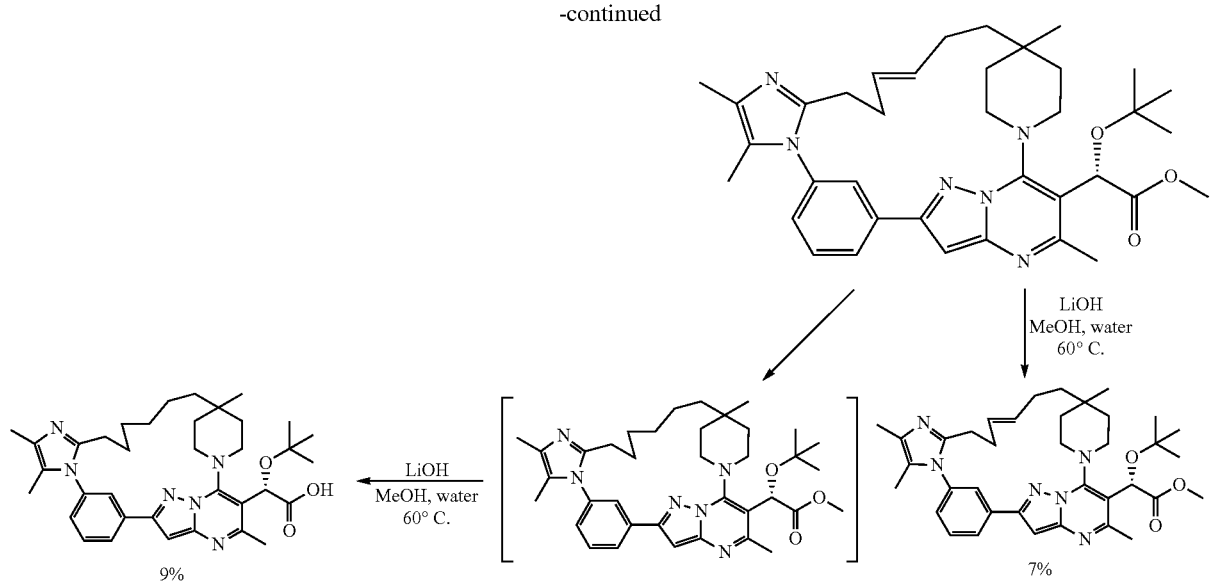

Intermediate 34

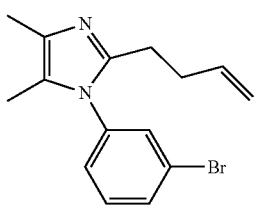 [SMILES: C=CCCc1nc(C)c(C)n1-c1cccc(Br)c1]

1-(3-Bromophenyl)-2-(but-3-en-1-yl)-4,5-dimethyl-1H-imidazole: A solution of 3-bromoaniline (3.24 mL, 29.7 mmol, 1 equiv), 2,3-butadione (5.17 mL, 59.4 mmol, 2 equiv), 4-pentenal (5.87 mL, 59.4 mmol, 2 equiv), and NH$_4$OAc (4.58 g, 59.4 mmol, 2 equiv) in EtOH (150 mL) was heated at reflux for 3 h. Upon cooling to ambient temperature, the mixture was concentrated in vacuo. The residue was treated with 1 N NaOH and extracted with DCM (×3). The combined DCM extracts were dried (Na$_2$SO$_4$) and concentrated in vacuo. The crude product was purified by flash column chromatography (0-25% EtOAc in hexane) to provide the product (3.7 g, 41%). $^1$H NMR (400 MHz, CDCl$_3$) δ 7.66-7.57 (m, 1H), 7.42-7.34 (m, 2H), 7.17-7.12 (m, 1H), 5.76 (ddt, J=17.0, 10.3, 6.7 Hz, 1H), 5.01-4.90 (m, 2H), 2.59-2.52 (m, 2H), 2.42-2.34 (m, 2H), 2.20 (d, J=0.8 Hz, 3H), 1.93 (s, 3H); LCMS (ESI, M+1): 305.05.

Intermediate 35

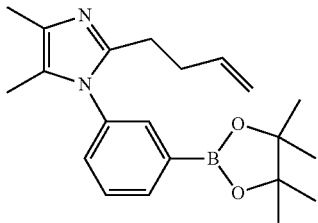

2-(But-3-en-1-yl)-4,5-dimethyl-1-(3-(4,4,5,5-tetramethyl-1,3,2-dioxaborolan-2-yl)phenyl)-1H-imidazole: To a solution of 1-(3-Bromophenyl)-2-(but-3-en-1-yl)-4,5-dimethyl-1H-imidazole (120 mg, 0.393 mmol, 1 equiv), 4,4,4',4',5,5,5',5'-octamethyl-2,2'-bi(1,3,2-dioxaborolane) (150 mg, 0.59 mmol, 1.5 equiv), and KOAc (77 mg, 0.79 mmol, 2 equiv) in 1,4-dioxane (1.6 mL) was added (dppf) PdCl$_2$.CH$_2$Cl$_2$ (32 mg, 0.039 mmol, 0.1 equiv). The mixture was heated to reflux for 2 h. Upon cooling to ambient temperature, the reaction was diluted with water (50 mL) and EtOAc (50 mL) and filtered through Celite. The aqueous phase was further extracted with EtOAc (2×50 mL). The combined EtOAc extracts were washed with brine, dried (Na$_2$SO$_4$) and concentrated in vacuo to provide the crude product. (0.10 g, 72%) as pale yellow oil that was used without further purification. LCMS (ESI, M+1): 353.25.

Intermediate 36

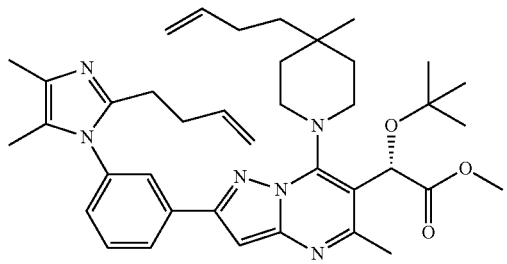

(S)-Methyl 2-(2-(3-(2-(but-3-en-1-yl)-4,5-dimethyl-1H-imidazol-1-yl)phenyl)-7-(4-(but-3-en-1-yl)-4-methylpiperidin-1-yl)-5-methylpyrazolo[1,5-a]pyrimidin-6-yl)-2-(tert-butoxy)acetate: A solution of 2-(but-3-en-1-yl)-4,5-dimethyl-1-(3-(4,4,5,5-tetramethyl-1,3,2-dioxaborolan-2-yl)phenyl)-1H-imidazole (104 mg, 0.295 mmol, 1.5 equiv), (S)-methyl 2-(2-bromo-7-(4-(but-3-en-1-yl)-4-methylpiperidin-1-yl)-5-methylpyrazolo [1,5-a]pyrimidin-6-yl)-2-(tert-butoxy)acetate (100 mg, 0.197 mmol, 1 equiv), PdCl$_2$ (dppf)-CH$_2$Cl$_2$ adduct (16 mg, 0.02 mmol, 0.1 equiv), and K$_3$PO$_4$ (0.30 mL of a 2 N aqueous solution, 0.591 mmol, 3 equiv) in DMF (2 mL) was heated at 85° C. for 30 min. Upon cooling to ambient temperature, the reaction was added to saturated aqueous NaHCO$_3$ and extracted with EtOAc (×3). The combined EtOAc extracts were dried (Na$_2$SO$_4$) and concentrated in vacuo to provide the crude product The crude product was purified by flash column chromatography (0-10% MeOH in DCM) to provide the product (80 mg, 89% yield). LCMS (ESI, M+1): 653.4.

Intermediate 37

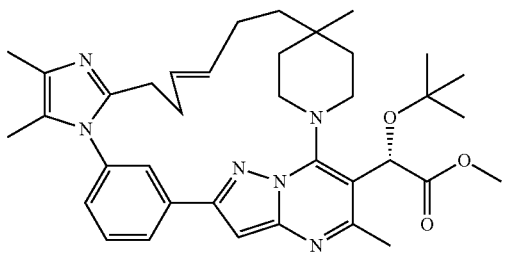

Methyl (2S)-tert-butoxy[4,16,17,26-tetramethyl-1,5,7,8,15,18-hexaazahexacyclo[24.2.2.1$^{6,9}$.1$^{10,14}$.0$^{2,7}$.0$^{15,19}$]dotriaconta-2,4,6(32),8,10(31),11,13,16,18,22-decaen-3-yl]acetate: A (S)-methyl 2-(2-(3-(2-(but-3-en-1-yl)-4,5-dimethyl-1H-imidazol-1-yl)phenyl)-7-(4-(but-3-en-1-yl)-4-methylpiperidin-1-yl)-5-methylpyrazolo[1,5-a]pyrimidin-6-yl)-2-(tert-butoxy)acetate (40 mg, 0.061 mmol, 1 equiv) and TsOH (11.65 mg, 0.061 mmol, 1 equiv) in DCE (30 mL) was heated to 90° C. The Hoyveda Grubbs 2$^{nd}$ generation catalyst (7.68 mg, 0.012 mmol, 0.2 equiv) was added. The pale green brown solution was stirred for 3 h and then allowed to cool to ambient temperature. The solution was washed with saturated aqueous NaHCO$_3$ solution. The DCE layer was dried (MgSO$_4$) and concentrated in vacuo. The crude product was used without further purification. LCMS (ESI, M+1): 625.4.

Example 9

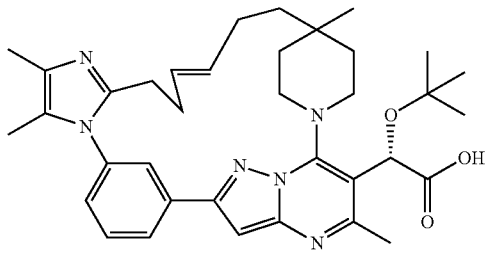 [SMILES: Cc1nc2cc3nn2c(c1[C@H](OC(C)(C)C)C(=O)O)N1CCC(C)(CC/C=C/CCc2nc(C)c(C)n2-c2cccc-3c2)CC1]

(2S)-tert-Butoxy[4,16,17,26-tetramethyl-1,5,7,8,15,18-hexaazahexacyclo[24.2.2.1$^{6,9}$.1$^{10,14}$.0$^{2,7}$.0$^{15,19}$]dotriaconta-2,4,6(32),8,10(31),11,13,16,18,22-decaen-3-yl]acetic acid: The crude product from above, methyl (2S)-tert-butoxy[4,16,17,26-tetramethyl-1,5,7,8,15,18-hexaazahexacyclo [24.2.2.1$^{6,9}$.1$^{10,14}$.0$^{2,7}$.0$^{15,19}$]dotriaconta-2,4,6(32),8,10 (31),11,13,16,18,22-decaen-3-yl]acetate (15 mg, 0.024 mmol, 1 equiv) was dissolved in MeOH (1 mL) and LiOH.H$_2$O (58 mg, 1.45 mmol, 60 equiv) was added. The reaction was heated to 60° C. for 2 h. Upon cooling to ambient temperature, the reaction was filtered and purified via preparative LC/MS with the following conditions: Column: XBridge C18, 19×mm, 5-μm particles; Mobile Phase A: 5:95 methanol: water with 10-mM ammonium acetate; Mobile Phase B: 95:5 methanol: water with 10-mM ammonium acetate; Gradient: 60-100% B over 20 minutes, then a 5-minute hold at 100% B; Flow: 20 mL/min. Product isolated (1.0 mg, 7% over 2 steps). $^1$H NMR (400 MHz, CD$_3$OD) δ 8.04 (d, J=7.5 Hz, 1H), 7.97 (d, J=11.3 Hz, 1H), 7.69 (t, J=7.9 Hz, 1H), 7.27 (d, J=7.8 Hz, 1H), 6.88 (br. s., 1H), 5.94 (br. s., 1H), 5.53 (br. s., 1H), 5.33 (d, J=15.1 Hz, 1H), 4.67-4.13 (m, 1H), 3.74 (br. s., 1H), 2.77 (br. s., 2H), 2.68 (s, 3H), 2.57-2.31 (m, 2H), 2.23 (s, 3H), 1.88 (s, 3H), 1.79-1.48 (m, 10H), 1.27 (s, 9H), 0.98 (s, 3H); LCMS (ESI, M): 610.4.

Example 10

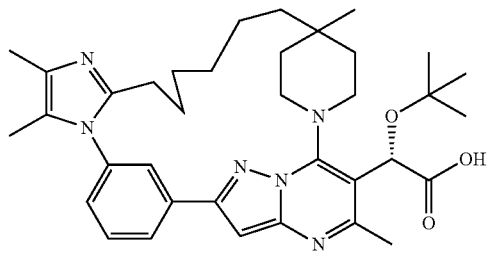 [SMILES: Cc1nc2cc3nn2c(c1[C@H](OC(C)(C)C)C(=O)O)N1CCC(C)(CCCCCCc2nc(C)c(C)n2-c2cccc-3c2)CC1]

(2S)-tert-Butoxy[4,16,17,26-tetramethyl-1,5,7,8,15,18-hexaazahexacyclo[24.2.2.1$^{6,9}$.1$^{10,14}$.0$^{2,7}$.0$^{15,19}$]dotriaconta-2,4,6(32),8,10(31),11,13,16,18-nonaen-3-yl]acetic acid: The crude product from above, methyl (2S)-tert-butoxy[4,16,17,26-tetramethyl-1,5,7,8,15,18-hexaazahexacyclo[24.2.2.1$^{6,9}$.1$^{10,14}$.0$^{2,7}$.0$^{15,19}$]dotriaconta-2,4,6(32),8,10(31),11,13,16,18,22-decaen-3-yl]acetate (15 mg, 0.024 mmol, 1 equiv) (10 mg, 0.016 mmol, 1 equiv) was dissolved in MeOH (1 mL). 10% Pd/C (2 mg, 0.0016 mmol, 0.1 equiv) was added and reaction was put under a balloon of H$_2$ for 2 h. Upon completion, the reaction was filtered through celite. To the MeOH filtrate was added LiOH.H$_2$O (38 mg, 1.45 mmol, 60 equiv) was added. The reaction was heated to 60° C. for 2 h. Upon cooling to ambient temperature, the reaction was filtered and purified via preparative LC/MS with the following conditions: Column: XBridge C18, 19×200 mm, 5-μm particles; Mobile Phase A: 5:95 acetonitrile: water with 10-mM ammonium acetate; Mobile Phase B: 95:5 acetonitrile: water with 10-mM ammonium acetate; Gradient: 30-70% B over 20 minutes, then a 5-minute hold at 100% B; Flow: 20 mL/min. Product isolated (0.9 mg, 9% over 2 steps). $^1$H NMR (400 MHz, CD$_3$OD) δ 8.06 (d, J=8.0 Hz, 1H), 7.98 (d, J=5.0 Hz, 1H), 7.71 (t, J=7.8 Hz, 1H), 7.30 (d, J=8.5 Hz, 1H), 6.88 (s, 1H), 5.83 (br. s., 1H), 4.63 (br. s., 1H), 3.68 (d, J=6.0 Hz, 1H), 3.57-3.46 (m, 1H), 2.78 (d, J=16.8 Hz, 1H), 2.66 (s, 3H), 2.52 (d, J=7.8 Hz, 1H), 2.25 (s, 3H), 1.97 (s, 3H), 1.82-1.29 (m, 15H), 1.26 (s, 9H), 0.98 (s, 3H); LCMS (ESI, M): 612.4.

It will be evident to one skilled in the art that the present disclosure is not limited to the foregoing illustrative examples, and that it can be embodied in other specific forms without departing from the essential attributes thereof. It is therefore desired that the examples be considered in all respects as illustrative and not restrictive, reference being made to the appended claims, rather than to the foregoing examples, and all changes which come within the meaning and range of equivalency of the claims are therefore intended to be embraced therein.

We claim:
1. A compound of Formula I

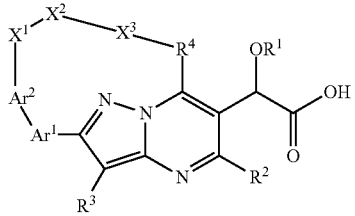

where:
R[1] is hydrogen, alkyl, or cycloalkyl;
R[2] is hydrogen or alkyl;
R[3] is hydrogen, alkyl or halo;
R[4] is azetidinyl, pyrrolidinyl, piperidinyl, piperazinyl, morpholinyl, homopiperidinyl, homopiperazinyl, or homomorpholinyl, and is substituted with 0-3 halo or alkyl substituents;
R[5] is hydrogen or alkyl;
Ar[1] is phenyl substituted with 0-3 substituents selected from cyano, halo, alkyl, haloalkyl, alkoxy, and haloalkoxy;
Ar[2] is pyrrolyl, furanyl, thienyl, pyrazolyl, isoxazolyl, isothiazolyl, imidazolyl, oxazolyl, thiazolyl, triazolyl, oxadiazolyl, or thiadiazolyl, and is substituted with 0-3 alkyl substituents;
$X^1$ is CH, $CH_2$, O, S, or $NR^5$;
$X^2$ is alkylene or alkenylene; and
$X^3$ is CH, $CH_2$, $CH_2O$, O, S, or $NR^5$;
or a pharmaceutically acceptable salt thereof.

2. A compound of claim 1 where R[1] is alkyl; R[2] is alkyl; R[3] is hydrogen; R[4] is azetidinyl, pyrrolidinyl, piperidinyl, piperazinyl, morpholinyl, homopiperidinyl, homopiperazinyl, or homomorpholinyl substituted with 0-3 alkyl substituents; Ar[1] is phenyl substituted with 0-3 substituents selected from cyano, halo, alkyl, haloalkyl, alkoxy, and haloalkoxy; Ar[2] is pyrrolyl, furanyl, thienyl, pyrazolyl, isoxazolyl, isothiazolyl, imidazolyl, oxazolyl, thiazolyl, triazolyl, oxadiazolyl, or thiadiazolyl, and is substituted with 0-3 alkyl substituents; $X^1$ is $CH_2$ or O; $X^2$ is alkylene or alkenylene; and $X^3$ is CH, $CH_2$ or O; or a pharmaceutically acceptable salt thereof.

3. A compound of claim 2 where R[4] is piperidinyl substituted with 0-1 alkyl substituents; Ar[1] is phenyl; Ar[2] is pyrazolyl, imidazolyl, or thiazolyl substituted with 0-3 alkyl substituents; $X^1$ is $CH_2$ or O; $X^2$ is alkylene or alkenylene; and $X^3$ is CH, $CH_2$ or O; or a pharmaceutically acceptable salt thereof.

4. A compound of claim 1 where R[1] is alkyl, R[2] is alkyl and R[3] is hydrogen.

5. A compound of claim 1 where R[4] is piperidinyl substituted with 0-3 alkyl substituents.

6. A compound of claim 1 where Ar[1] is phenyl.

7. A compound of claim 1 where Ar[2] is pyrazolyl, imidazolyl, or thiazolyl substituted with 0-3 alkyl substituents.

8. A compound of claim 1 $X^1$ is $CH_2$ or O; $X^2$ is alkylene or alkenylene; and $X^3$ is CH, $CH_2$ or O.

9. A compound of claim 1 where $X^1$ is $CH_2$; $X^2$ is alkylene or alkenylene; and $X^3$ is $CH_2$.

10. A compound of claim 1 selected from the group consisting of
(2S)-tert-Butoxy[(21E)-4,25-dimethyl-24-oxa-1,5,7,8,15,30-hexaazahexacyclo[23.2.2.1$^{6,9}$.1$^{10,14}$.1$^{15,18}$.0$^{2,7}$]dotriaconta-2,4,6(32),8,10(31),11,13,16,18(30),21-decaen-3-yl]acetic acid;
(2S)-tert-Butoxy[4,25-dimethyl-24-oxa-1,5,7,8,15,30-hexaazahexacyclo[23.2.2.1$^{6,9}$.1$^{10,14}$.1$^{15,18}$.0$^{2,7}$]dotriaconta-2,4,6(32),8,10(31),11,13,16,18(30)-nonaen-3-yl]acetic acid;
(2S)-tert-Butoxy[4,25-dimethyl-24-oxa-1,5,7,8,18,30-hexaazahexacyclo[23.2.2.1$^{6,9}$.1$^{10,14}$.1$^{15,18}$.0$^{2,7}$]dotriaconta-2,4,6(32),8,10(31),11,13,15(30),16-nonaen-3-yl]acetic acid;
(2S)-tert-Butoxy[4,24-dimethyl-23-oxa-1,5,7,8,18,29-hexaazahexacyclo[22.2.2.1$^{6,9}$.1$^{10,14}$.1$^{15,18}$.0$^{2,7}$]hentriaconta-2,4,6(31),8,10(30),11,13,15(29),16-nonaen-3-yl]acetic acid;
(2S)-tert-Butoxy[4,17,26-trimethyl-1,5,7,8,15,16-hexaazahexacyclo[24.2.2.1$^{6,9}$.1$^{10,14}$.0$^{2,7}$.0$^{15,19}$]dotriaconta-2,4,6(32),8,10(31),11,13,16,18-nonaen-3-yl]acetic acid;
(2S)-tert-Butoxy[4,17,25-trimethyl-1,5,7,8,15,16-hexaazahexacyclo[23.2.2.1$^{6,9}$.1$^{10,14}$.0$^{2,7}$.0$^{15,19}$]hentriaconta-2,4,6(31),8,10(30),11,13,16,18-nonaen-3-yl]acetic acid;
(2S)-tert-Butoxy[4,17,26-trimethyl-18-thia-1,5,7,8,16-pentaazahexacyclo[24.2.2.1$^{6,9}$.1$^{10,14}$.0$^{2,7}$.0$^{15,19}$]dotriaconta-2,4,6(32),8,10(31),11,13,15(19),16-nonaen-3-yl]acetic acid;
(2S)-tert-Butoxy[4,17,25-trimethyl-18-thia-1,5,7,8,16-pentaazahexacyclo[23.2.2.1$^{6,9}$.1$^{10,14}$.0$^{2,7}$.0$^{15,19}$]hentriaconta-2,4,6(31),8,10(30),11,13,15(19),16-nonaen-3-yl]acetic acid;
(2S)-tert-Butoxy[4,16,17,26-tetramethyl-1,5,7,8,15,18-hexaazahexacyclo[24.2.2.1$^{6,9}$.1$^{10,14}$.0$^{2,7}$.0$^{15,19}$]dotriaconta-2,4,6(32),8,10(31),11,13,16,18,22-decaen-3-yl]acetic acid; and
(2S)-tert-Butoxy[4,16,17,26-tetramethyl-1,5,7,8,15,18-hexaazahexacyclo[24.2.2.1$^{6,9}$.1$^{10,14}$.0$^{2,7}$.0$^{15,19}$]dotriaconta-2,4,6(32),8,10(31),11,13,16,18-nonaen-3-yl]acetic acid
or a pharmaceutically acceptable salt thereof.

11. A composition useful for treating HIV infection comprising a therapeutic amount of a compound of claim 1 and a pharmaceutically acceptable carrier.

12. A method for treating HIV infection comprising administering a therapeutically effective amount of a compound of claim 1, or a pharmaceutically acceptable salt thereof, to a patient in need thereof.

* * * * *